United States Patent [19]

Maekawa et al.

[11] Patent Number: 5,644,388
[45] Date of Patent: Jul. 1, 1997

[54] IMAGING FLOW CYTOMETER NEARLY SIMULTANEOUSLY CAPTURING A PLURALITY OF IMAGES

[75] Inventors: Yasunori Maekawa, Miki; Tokihiro Kosaka, Kakogawa, both of Japan

[73] Assignee: Toa Medical Electronics Co., Ltd., Hyogo, Japan

[21] Appl. No.: 424,076

[22] Filed: Apr. 19, 1995

[30] Foreign Application Priority Data

Apr. 19, 1994 [JP] Japan .................................. 6-080509

[51] Int. Cl.$^6$ .................... G01N 21/00; G01N 33/48; G01J 3/30
[52] U.S. Cl. .................... 356/73; 356/39; 356/316; 356/338; 382/134
[58] Field of Search .................... 356/73, 338–339, 356/39–40, 316–317; 302/133–134

[56] References Cited

U.S. PATENT DOCUMENTS

| | | | |
|---|---|---|---|
| 5,159,397 | 10/1992 | Kosaka et al. | 356/73 |
| 5,159,398 | 10/1992 | Maekawa et al. | 356/73 |
| 5,247,339 | 9/1993 | Ogino | 356/73 |
| 5,247,348 | 9/1993 | Ogino | 356/73 |
| 5,428,441 | 6/1995 | Ogino et al. | 356/73 |
| 5,448,349 | 9/1995 | Kosaka | 356/73 |
| 5,471,294 | 11/1995 | Ogino | 356/73 |
| 5,521,699 | 5/1996 | Kosaka et al. | 356/73 |

FOREIGN PATENT DOCUMENTS

| | | |
|---|---|---|
| 3105235 | 5/1991 | Japan . |
| 5119035 | 5/1993 | Japan . |

OTHER PUBLICATIONS

Kachel, Volker Cell Analysis, vol. 1, "The Electrical Resistance Pulse Technique", pp. 306–313, 1982.

"Fluorescent in situ hybridization"; Human Cell 2(4), Apr. 2, 1989; Dr. Toru Yasutake, First Dept. of Surgery, Nagasaki University School of Medicine, 7-1 Sakamoto, Nagasaki 853 Japan; pp. 436–438.

*Primary Examiner*—Frank Gonzalez
*Assistant Examiner*—Jason D. Vierra Eisenberg

[57] ABSTRACT

A sample liquid containing particles are caused to flow through a transparent flow cell. An image capturing device is used to capture different images for a single particle existing in an image capturing area of the flow cell. The image capturing device further preferably captures different images of the single particle from different directions. Further, the image capturing device can capture different images at different focal positions. The different images can include fluorescence images and chemiluminescence images.

21 Claims, 17 Drawing Sheets

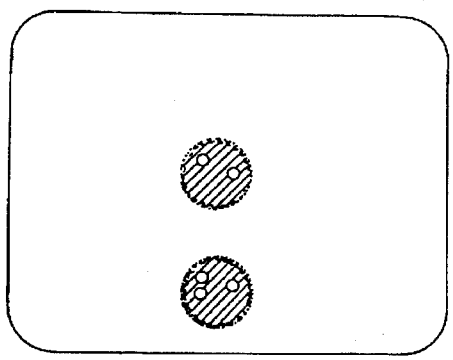
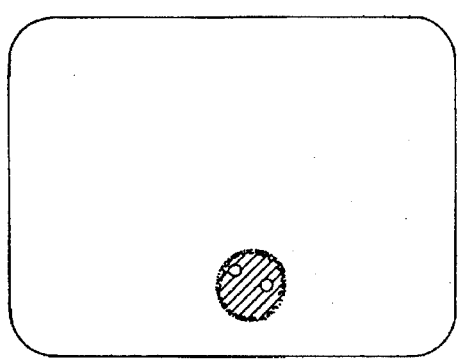
FIG. 2(a)  FIG. 2(b)
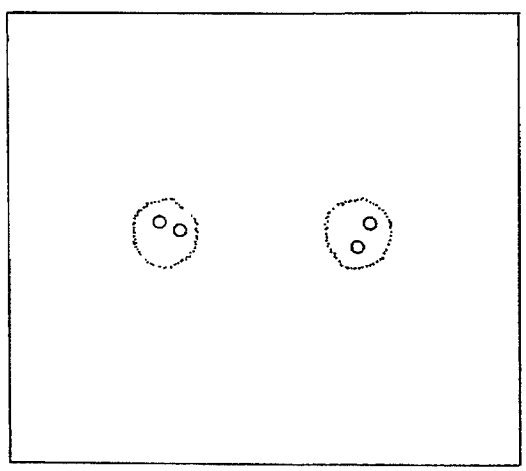
FIG. 10
FIG. 14(a)  FIG. 14(b)
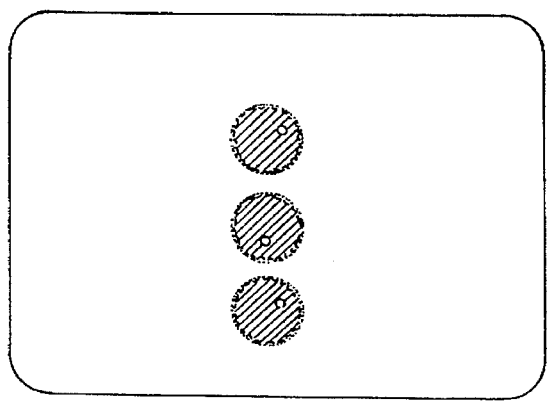
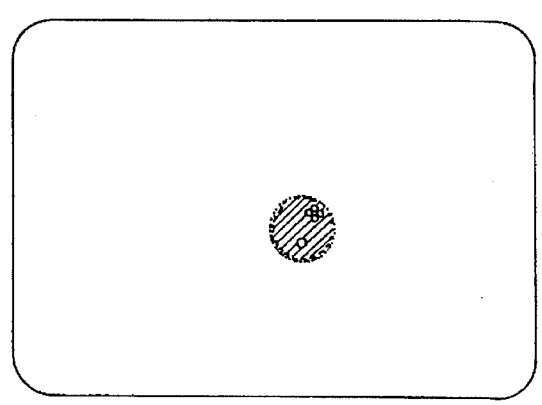

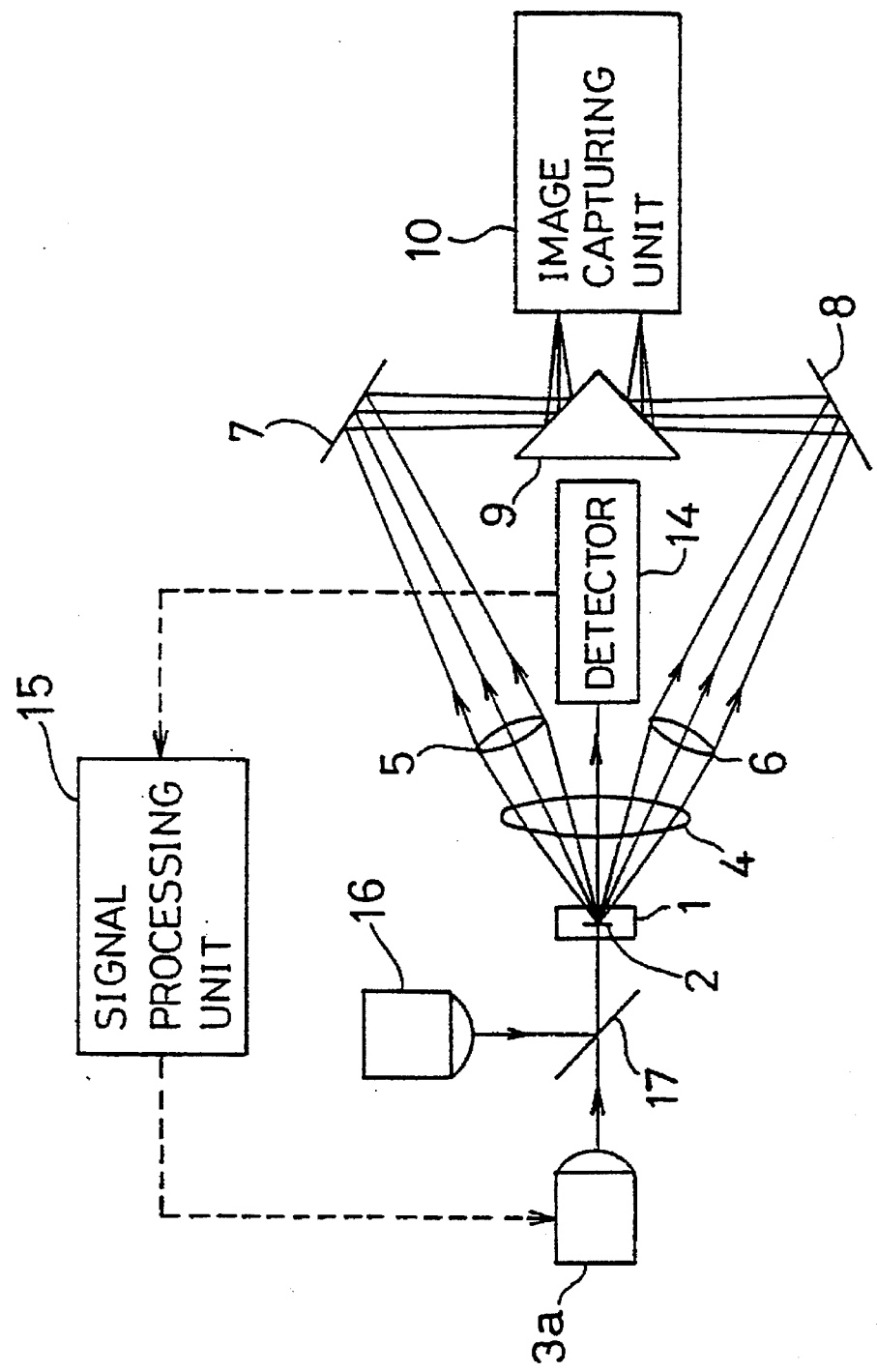

IMAGING FLOW CYTOMETER NEARLY SIMULTANEOUSLY CAPTURING A PLURALITY OF IMAGES

BACKGROUND OF THE INVENTION

1. Field of the Invention

The present invention relates to an imaging flow cytometer. More specifically, the invention relates to an imaging flow cytometer in which, for instance, to detect a particular substance in a cell or a microorganism, a suspension (called a sample liquid) of cells or microorganisms that have been reacted with a fluorescence-dyed or fluorescence-marked monoclonal antibody or DNA probe, for instance, is introduced into a thin glass tube, and a fluorescence image of a cell, a microorganism is taken by a flow scheme and analyzed.

2. Description of the Related Art

In recent years, molecular-biological analyses and tests have been widely conducted for diagnoses of cancer, hereditary diseases, etc. and analyses of cell dynamism. For example, to detect a particular substance (DNA, a propagative antigen, HBsAg, a cancer gene product, or the like) included in a cell, blood cell, or the like, or to conduct a test for abnormality in the number of chromosomes, cells are processed using a specific reaction reagent that is a fluorescence-marked monoclonal antibody, chromosome-specific DNA probe, or the like and fluorescence images of such cells are examined with a fluorescence microscope.

To evaluate the safety of medical supplies, food additives, etc., micronucleus tests have been conducted to check existence of fragments (micronuclei) that are produced by abnormal chromosomes. In the micronucleus test, micronuclei remaining in blood cells are subjected to fluorescence dying and the existence of micronuclei is checked using a fluorescence microscope, or the like.

Further, to test the degree of voraciousness of white blood cells, beads marked by a fluorescent substance have been caused to be gormandized by white blood cells and the number of beads is counted using fluorescent images.

Conventionally, since the above measurements have been performed by using a fluorescence microscope, much time and labor was needed if a large number of cells or blood cells were involved.

In a measurement using a fluorescence microscope, a small depth of field is not a serious problem in the case where cells develops on a slide glass. However, in a measurement on a sample in which a cell-floating liquid is sealed in a slide glass, a small depth of field needs to be compensated such that a measurer observes cells at every point along the optical axis while varying the focal point of a microscope.

Recently, it was attempted to automatize the above analyses and tests by combining a fluorescence microscope and an image processing device. However, it took long time for such an apparatus to analyze a number of cells. Although measurements using the conventional flow cytometer (FCM) were also attempted, this method could not provide information on the locality of a part emitting fluorescence. In addition, the measurement accuracy was affected by background fluorescence (unspecific fluorescence) from parts other than a part where a specific substance to be detected existed. Therefore, this method has not been put to practical use yet.

To solve the above problems, an apparatus called a fluorescence image capturing type imaging flow cytometer (IFCM) has been put to practical use. In this apparatus, a suspension of cells or microorganisms that have been reacted with a specific fluorescence-dyed or fluorescence-marked monoclonal antibody or DNA probe is introduced into a thin glass tube, and fluorescence images of the cells or microorganisms are taken and subjected to analysis.

However, where this apparatus is applied to the above measurements, due to a small depth of field, it is difficult for this apparatus to measure, with high accuracy, light emitting points that are distributed three-dimensionally in a cell.

Therefore, various attempts are made to overcome the small depth of field. One example is a method of increasing the depth of field (i.e., obtaining a larger depth of field) optically. In this method, NA of an image-forming optics is set as small as possible; for example, a depth of field of more than 12 μm is obtained with NA of 0.25. However, this method cannot secure three-dimensional resolution because, for instance, two light emitting points arranged parallel with the optical axis are superimposed and observed as a single light emitting point. That is, light emitting points cannot be counted correctly, meaning lowered measurement accuracy.

There is a paper relating to this invention: "Study of Fluorescence in situ Hybridization for Detection of Chromosome Aberration," Human Cell 2(4), pp. 436–438, 1989. The abstract of this paper states "The authors applied fluorescence in situ hybridization (FISH) technique for the detection of chromosome aberration in interphase nuclei using the probe specific to alphoid repeats on chromosome 11 and X. Chromosome 11 specific probe showed two major spots in lymphocyte nuclei, while X specific probe showed single spot in male and double spots in female respectively. On the other hand three spots were detected in most of the nuclei from HeLa cells with 11 and X specific probes. We concluded that FISH with the use of chromosome specific probe may become a useful and reliable tool for the detection of chromosome aberration in interphase nuclei."

Further, a disclosure to the effect that a plurality of particle images of a single cell are taken at different time points with different focal positions is found in Cell Analysis, Vol. 1, pp. 306–313, 1982.

SUMMARY OF THE INVENTION

An object of the present invention is to provide an imaging flow cytometer which can positively capture and correctly count minute light emitting points that are distributed three-dimensionally in a cell (particle) by taking a plurality of different images (for instance, fluorescence images or chemiluminescence images) of a single cell, producing a plurality of different images on a single screen. Further, image analysis is performed to secure resolution of fluorescence images which is required for application to a testing apparatus that is used for, for instance, a test of abnormality in the number of chromosomes and a micronucleus test for evaluation of the safety of medical supplies, or a testing apparatus for the degree of voraciousness of white blood cells. In this case, chemiluminescence images may be taken by subjecting cells (particles) to a treatment for cause chemiluminescence.

The invention provides an imaging flow cytometer comprising a transparent flow cell through which a sample liquid containing particles is caused to flow, and image capturing device for capturing different images for a single particle existing in an image capturing area of the flow cell.

These and other objects of the present application will become more readily apparent from the detailed description given hereinafter. However, it should be understood that the preferred embodiments of the invention are given by way of illustration only, since various changes and modifications within the spirit and scope of the invention will become apparent to those skilled in the art from this detailed description.

BRIEF DESCRIPTION OF THE DRAWINGS

FIGS. 2(a) and 2(b) show examples of imaging screens;

FIG. 5 shows an embodiment of taking transmission light images;

FIG. 10 an example of a fluorescence imaging screen;

FIGS. 14(a) and 14(b) show examples of imaging screens;

FIGS. 19(a) and 19(b) show another example of detecting overlapping of cells in the case where a line sensor is used.

DESCRIPTION OF THE PREFERRED EMBODIMENTS

Figure 1:
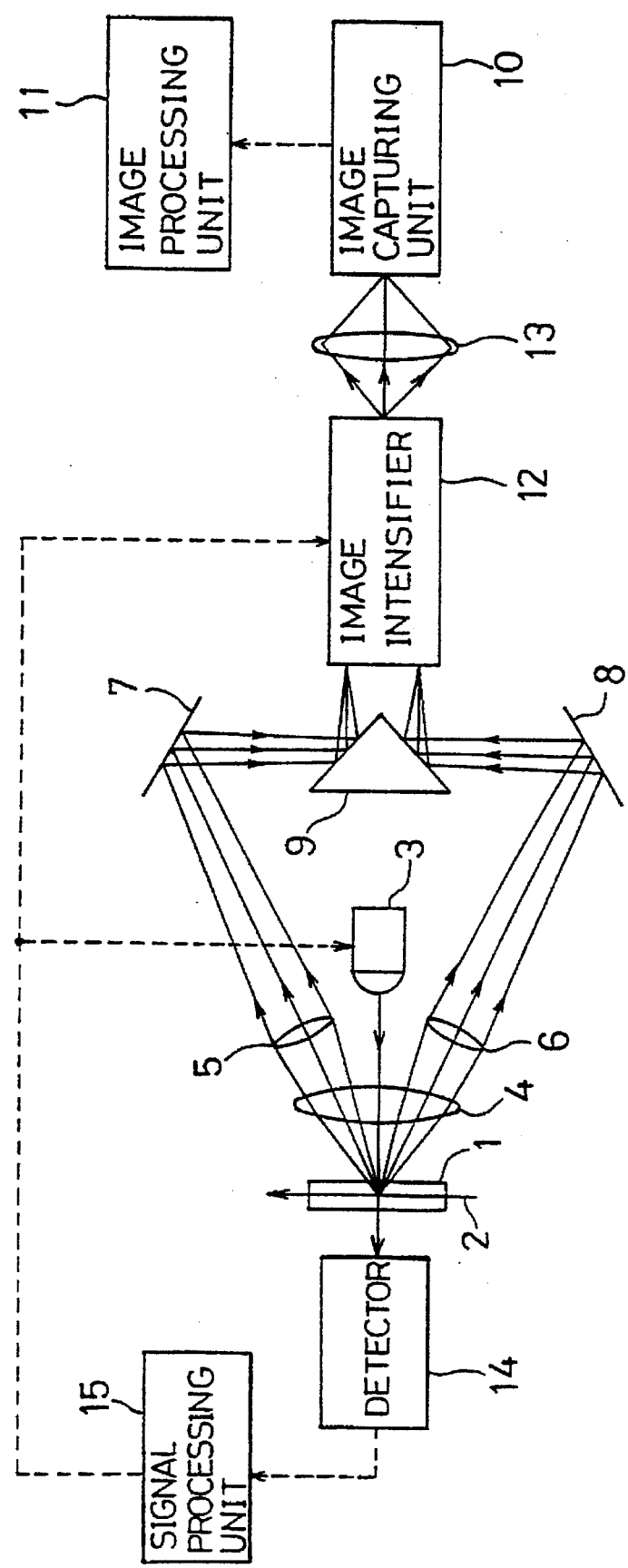
FIG. 1 shows a configuration of an imaging flow cytometer according to Embodiment 1 of the present invention.

One important feature of the present application is that, when taking images of particles, different images are captured for a single particle. That is, a plurality of images are taken for a single particle from different directions or with different focal positions, to thereby capture all light emitting points of chromosomes, micronuclei or beads that are distributed three-dimensionally in a cell. The image of a particle refers to a fluorescence image or a chemiluminescence image.

In the application, for example, a transparent tube made of glass or plastics, which enables imaging of particles from the outside of the flow cell, is used as the flow cell.

The flow cell my have a variety of shapes, that is, may have a circle cross-section (circular sheath), a rectangular or elliptical cross-section (planar sheath), etc. However, to obtain clear images of particles, it is necessary to take images of individual particles without superposition while keeping the focal position stable with respect to a particle. From this point of view, the planar sheathed flow cell having a rectangular or elliptical cross-section is suitable which can not only cause particles to flow in a separated state, but can also cause flat particles to flow being so oriented as to face the front side of the imaging direction. This type of flow cell may be a known one which allows formation of a flat sample liquid flow having a width of about 50–300 µm and a thickness of about ¹⁄₁₀ of the width. For example, the flow cell described in Japanese Unexamined Patent Publication No. Hei. 3-105235 may be used.

Mainly, a sample liquid prepared by diluting microorganism, blood or urine at an arbitrary ratio is introduced into the flow cell. No particular limitations are imposed on the material, specific gravity, shape, etc. of particles except that their sizes should allow them to be introduced into the flow cell. Particles may be microorganisms, blood cells contained in blood, cells contained in urine, etc.

Any image capturing device may be used which can capture images of particles existing in the image capturing area of the flow cell. For example, a video camera on the market can be used.

With the above configuration, it is possible to take an image of a minute light emitting portion such as a chromosome, micronucleus, or a bead in a particle, to enable highly accurate measurement.

In the imaging flow cytometer of the invention, the image capturing device may be so constructed as to take a plurality of particle images of a single particle from a plurality of directions. Alternatively, it may be so constructed as to simultaneously take a plurality of particle images of a single particle using a plurality of different focal positions. As a further alternative, it may be so constructed as to take a plurality of particle images of a single particle with different focal positions at different time points.

In the imaging flow cytometer of the invention, a fluorescence exciting light source for applying fluorescence excitation light to the image capturing area of the flow cell may be provided. In this case the image capturing device captures fluorescence images of a particle existing in the image capturing area of the flow cell.

As the fluorescence exciting light source, various light sources may be used which can apply light capable of production of fluorescence images of a particle to the image capturing area of the flow cell. However, because it is necessary to input condensed light to the small image capturing area where particles exist, a laser light source is suitable which outputs light that can be focused easily and has high intensity.

To take images of a particle without blurring, it is preferred that the fluorescence exciting light source be of a pulsed emission type. In the case of using a CW emission type light source, an optical shutter (or an electronic shutter) having a gating function (function of opening and closing an optical path leading to the image capturing device) is disposed, to take images of a particle without blurring. Where it is necessary to increase the intensity of a produced optical image, an image intensifier having a gating function is disposed before the image capturing device.

Further, in the imaging flow cytometer of the invention, to efficiently image particles, it is preferred that a particle passage monitoring system be added and a particle be imaged after entrance of a particle into the image capturing area is confirmed.

The particle passage monitoring system includes a detector for detecting passage of a particle.

The particle passage monitoring system may consist of a monitoring light source for constantly emitting light and applying light to a flow of the sample liquid in the flow cell. A detector is included for detecting, by use of light emitted from the monitoring light source, that a particle passes through the image capturing area of the flow cell. The monitoring light source may be a CW emission type light source such as a LD, LED, SLD, or the like.

Where the imaging flow cytometer of the invention is provided with the particle passage monitoring system and uses a CW emission type light source as the fluorescence exciting light source, the fluorescence exciting light source can also serve as the monitoring light source of the particle passage monitoring system.

In the imaging flow cytometer of the invention, it is preferred that particles contained in a sample liquid are preprocessed with a reagent for causing fluorescence. The reagent is to fluorescence-dye or fluorescence-mark a monoclonal antibody or a chromosome-specific DNA probe, or the like, each of which is a specific reaction reagent to detect a particular substance (DNA, a propagative antigen, HBsAg, a cancer gene product, or the like) contained in a cell, a blood cell, or the like. Usually, FITC and PI (propidium iodide) are used as the reagent.

In this case, the light source should be of a type which can apply fluorescence excitation light to the image capturing area of the flow cell. Ordinary laser light may be used as the fluorescence excitation light. The imaging capturing device takes images of a particle existing in the image capturing area of the flow cell using fluorescence that is generated in the above manner.

Where such particles as cells that emit light without being processed with a reagent are a measurement object, they need not be processed with the above reagent. Further, where particles that emit light by themselves without light illumination are a measurement object, they need not be illuminated. For example, chemiluminescence images may be taken by processing particles with a reagent for causing chemiluminescence. Where chemiluminescence is used in this manner, no light source is needed.

In the imaging flow cytometer of the invention, as described above, it is preferred to form a flat sheathed flow of a sample liquid in the flow cell. In this case, it is preferred that light emitted from the fluorescence exciting light source be input from the narrower width side of the sheathed flow.

That is, it is desired that the fluorescence excitation light be so input as to provide an elliptical illumination area having a major axis sufficiently longer than the longitudinal size of the image capturing area and a minor axis sufficiently longer than the thickness of particles to be imaged, and provide uniform intensity over the image capturing area.

With this scheme, since the excitation light can be narrowed in the flow cell thickness direction, the illumination intensity per unit area of the excitation light can be increased, to provide fluorescence images having large S/N ratios.

The present invention will be hereinafter described in detail by way of illustrated Embodiments 1 to 3.

Embodiment 1

FIG. 1 shows a configuration of an imaging flow cytometer according to Embodiment 1 of the invention.

In the imaging flow cytometer of this embodiment, a sample flow is formed by introducing a sample liquid that is prepared by diluting microorganisms, blood, urine, or the like into a transparent glass tube called a flow cell. Fluorescence images or transmission light images of particles (also called subject particles) such as blood cells contained in blood or cells contained in urine are taken by a video camera by applying pulse light such as strobe light or pulsed laser light or CW light to the sample flow.

In the following, the subject particle is described as a cell, which is a typical example. However, the subject particle is not limited to a cell, but includes a microorganism, a blood cell contained in blood, and other particles.

This embodiment is characterized in that two fluorescence images are taken simultaneously from two different directions.

Referring to FIG. 1, reference numeral 1 denotes a flow cell that is a flat tube made of glass or plastics, for instance. When a sample liquid 2 is introduced into the flow cell 1, a sheath liquid is also supplied so as to surround the sample liquid 2, so that a laminar flow (called a sheathed flow) of the sample liquid 2 and the sheath liquid goes through the flow cell 1.

The sample flow 2 that is introduced into the flow cell 1 in the above manner (surrounded by the sheath liquid) is thinned by the hydrodynamic effect, so that cells flow in a single line. To increase the amount of sample analyses per unit time, a flow cell is used whose flow path has a large aspect ratio. That is, the flow cell 1 is a planar sheathed flow cell having a rectangular or elliptical cross-section which can not only cause particles to flow in a separated state, but can also cause flat particles to flow so as to face the front side of the imaging direction. Thus, a flat sample liquid is formed.

A sample liquid in the flow cell 1 has a width (in the longer side direction) of 50–300 μm and a thickness (in the shorter side direction, i.e., in the imaging direction) of 5–30 μm, i.e., about 1/10 of the width.

To detect a particular substance (DNA, a propagative antigen, HBsAg, a cancer gene product, or the like) contained in a cell or to perform a test for abnormality in the number of chromosomes, cells in the flow cell 1 have been processed with a specific reaction reagent that is to fluorescence-mark a monoclonal antibody, a chromosome-specific DNA probe, or the like.

Reference numeral 3 denotes a light source for applying laser light to an image capturing area of the flow cell 1. Excited by the laser light, a fluorescent substance coupled to a particular substance (mentioned above) or a chromosome contained in a cell existing in the flow cell 1 emits light for a short time. (A particular substance or a chromosome contained in a cell is hereinafter referred to as a light emitting point or a fluorescence emitting portion.)

Since the light applied from the light source 3 serves to cause excitation for fluorescence, it is called excitation light. For the same reason, the light source 3 is called an exciting light source.

The exciting light source 3 is a CW emission type light source and, more specifically, a laser light emitting device capable of producing CW laser light. In FIG. 1, arrows indicate traveling directions of light.

Reference numeral 4 denotes a lens; 5, a first objective lens; 6, a second objective lens; 7, a first mirror; 8, a second mirror; and 9, a third mirror.

Reference numeral 10 denotes an image capturing unit constituted by a video camera. The image capturing unit 10 captures fluorescence images of a cell existing in the image capturing area of the flow cell 1. That is, the image capturing unit 10 captures fluorescence images of a cell that is excited by the excitation light applied from the exciting light source 3. The image capturing unit 10 has a photodetecting surface constituted of a CCD on which a fluorescence image of a cell is formed. Two fluorescence images produced by the two imaging optics are taken by the single video camera.

Reference numeral 11 denotes an image processing unit for performing various image processing on the fluorescence images taken by the image capturing unit 10. For example, the image processing unit 11 measures the number of fluorescence emitting portions, the size and position of a fluorescence emitting portion, or the shape (for instance, circularity) of a fluorescence emitting portion, or calculates a fluorescence emission quantity.

Reference numeral 12 denotes an image intensifier (hereinafter also referred to as I.I.) having a gating function (optical shutter function) for opening and closing the optical path leading to the image capturing unit 10. The image intensifier 12 serves as an optical amplifier for amplifying light intensity by a factor of about several tens of thousand. To capture an image of a cell without blurring, the image intensifier 12 is disposed before the image capturing unit 10, and opens the gate for a very short time in response to an external trigger signal. Reference numeral 13 denotes a relay lens 13. The relay lens 13 may be replaced by an optical fiber.

Reference numeral 14 denotes a cell passage monitoring detector for detecting a cell passing through the image capturing area of the flow cell 1. Constituted of a one-dimensional image sensor (line sensor) or a photodiode, the detector 14 detects light scattered by a cell. No cell passage monitoring light source is provided, because passage of a cell is monitored by using light originating from the exciting light source 3. That is, the exciting light source 3 also serves as the cell passage monitoring light source.

Reference numeral 15 denotes a signal processing unit for producing a trigger signal for opening the gate of the image intensifier 12 when passage of a cell is detected by the detector 14. The signal processing unit 15 confirms that a cell has entered the image capturing area, when the detector 14 detects scattered light. That is, the signal processing unit 15 judges whether to capture an image of the cell by comparing the intensity, pulse width, etc. of the scattered light detected by the detector 14 with values stored in advance. If the cell is one to be imaged, the signal processing unit 15 sends a signal for opening the gate to the image intensifier 12. For the selected imaging of cells, the method described in Japanese Unexamined Patent Publication No. Hei. 5-119035 can serve as a reference.

The cell passage monitoring system for detecting that a cell passes through the image capturing area of the flow cell 1 consists of the light source that emits light constantly (in this embodiment, the exciting light source 3 also serves as this light source) and the cell passage monitoring detector 14.

With the above configuration, a single cell is imaged from two different directions. Fluorescence beams obtained through the first and second objective lenses 5 and 6 are respectively reflected by the first and second mirrors 7 and 8, and further reflected by the third mirror 9, and fluorescence images are formed on one side of the photoelectric surface of the image intensifier 12. The two faint fluorescence images are amplified by the image intensifier 12 by a factor of about several tens of thousand, and taken by the image capturing unit 10 via the relay lens 13.

Actually, when the cell passage monitoring detector 14 detects that a cell to be imaged enters the image capturing area, the gate (optical shutter) of the image intensifier 12 is opened and the image intensifier 12 operates for a short, predetermined time to allow capturing of a fluorescence image without blurring. The fluorescence image taken by the image capturing unit 10 is sent, as a video signal, to the image processing unit 11 and processed there.

This embodiment can suppress the cost because two fluorescence images are taken by the one image intensifier 12 and the one video camera.

This embodiment is characterized in that two fluorescence images are taken for a single cell simultaneously from two different directions. With this scheme, even in the case of a cell having two fluorescence emitting points that are located one on another in the depth direction along the optical axis of the imaging optics, the two fluorescence emitting points can be discriminated from each other, to enable correct counting of light emitting points.

No specific limitation is imposed on the angle between the two directions of the imaging optics, but the angle may be so set as to be most suitable for each measurement object. Also no specific limitation is imposed on the angle of the imaging optics with respect to the cell flowing direction. However, the following setting is made in the case where it is necessary that cell images of any flowing cell always be taken from the same directions by the two imaging optics, to improve the measurement accuracy.

In the case of an ordinary sheathed flow in which a sample flow has a circular or square cross-section, there occurs no problem with any setting when the cell passage monitoring system is used, because cells are taken approximately at the same position. On the other hand, when no cell passage monitoring system is used, setting is made such that a plane defined by the axes of the two imaging optics is perpendicular to the axis of the sample flow.

In the case of a planar sheathed flow, when a linear cell passage monitoring system is used that crosses the sample flow (a cell is imaged on that line), the two imaging optics are set on a plane including the optical axes and the axis of the sample flow (see FIG. 1).

From the viewpoints of the measurement accuracy and the number of cells to be analyzed, a combination of the planar sheathed flow cell and the cell passage monitoring system is more practical.

FIGS. 2(a) and 2(b) show examples of imaging screens, which are fluorescence imaging screens obtained when a DNA probe subjected to a FISH treatment, i.e., fluorescence marking was hybridized with chromosomes, to perform a test for abnormality in the number of chromosomes. FIG. 2(a) shows an example of fluorescence images taken from two directions as in this embodiment, and FIG. 2(a) shows an example of a fluorescence image of the same cell as in FIG. 2(a) taken from only a single direction by the conventional IFCM.

In FIG. 2(a), the top image is one obtained through the first objective lens 5 in FIG. 1 and the bottom image is one obtained through the second objective lens 6. In this example, there are three light emitting points. Only two light emitting points are found in the top image, because the two left-hand light emitting points are located on each point along the optical axis. However, since three light emitting points are found in the bottom image that was taken from the different angle, it is concluded that the cell has three light emitting points.

The existence of the three light emitting points cannot be recognized from the image of FIG. 2(b), which is the same as the top image of FIG. 2(a).

Although the cell passage monitoring system is provided in this embodiment, the invention can be practiced even without it. However, the omission of the cell passage monitoring system is not practical in terms of the imaging efficiency and the measurement accuracy (refer to the above description relating to the imaging angle). Although in this embodiment the exciting light source 3 also serves as the cell passage monitoring light source, the latter may be provided separately.

Where the cell passage monitoring light source is provided separately, the exciting light source 3 may be a pulsed light source such as a pulsed laser or a Xe flash lamp, in which case the image intensifier 12 may be an ordinary one that is not equipped with a gate. Where fluorescence is very strong, it can be imaged by only the ordinary video camera without using the image intensifier 12.

Figure 3:
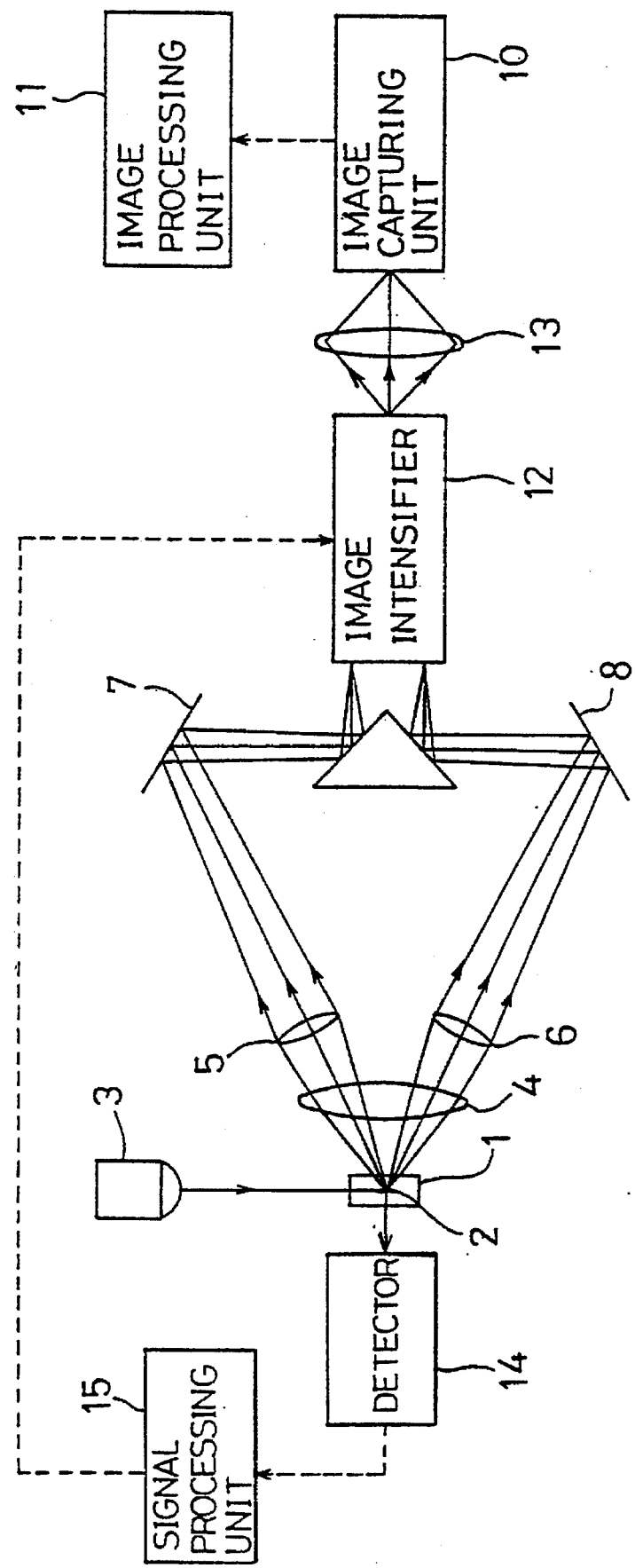
FIG. 3 shows an embodiment in which excitation light is applied from the side of a flow cell.

In the above embodiment, the excitation light is applied to the flow cell 1 from the back of the flow cell (hereinafter called a back illumination scheme). However, in this scheme, the density of illumination light has a certain limit, because the excitation light should be applied uniformly to the entire image capturing area. To solve this problem, the excitation light may be applied from the side of the flow cell 1 as shown in FIG. 3. In FIG. 3, the sample liquid 2 flows in the direction perpendicular to the paper surface.

Figure 4:
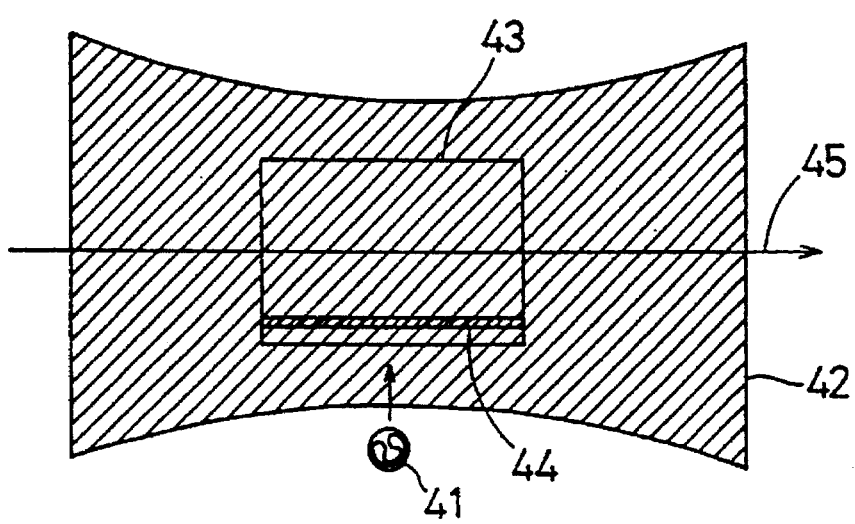
FIGS. 4(a) and 4(b) show how excitation light is applied to an image capturing area and its neighborhood in the case where it is applied from the side of the flow cell.
Figure 4B:
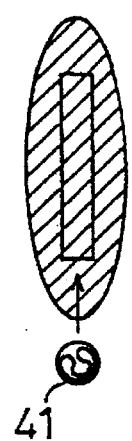

FIGS. 4(a) and 4(b) show how the excitation light is applied to the image capturing area and its neighborhood in the case where it is applied from the side of the flow cell 1 (hereinafter called a side illumination scheme). FIG. 4(a) shows an excitation light illumination area, and FIG. 4(b) is a sectional view showing the central portion of the excitation light illumination area. In FIGS. 4(a) and 4(b), reference numeral 41 denotes a cell; 42, the excitation light illumination area; 43, the image capturing area; 44, a cell passage monitoring area. Arrow 45 indicates an application direction of the excitation light.

The excitation light has an elliptical shape in which the major axis is sufficiently longer than the longitudinal size of the image capturing area 43 and the minor axis is sufficiently longer than the thickness of particles to be imaged, and is so applied as to provide uniform illumination intensity over the image capturing area 43. With this scheme, since the excitation light can be narrowed in the thickness direction of the flow cell 1, the illumination intensity per unit area of the excitation light can be increased, to enable production of fluorescence images having large S/N ratios. If the image capturing area 43 is restricted to a certain area, for instance, an area close to the cell passage monitoring area 44, the excitation light can further be narrowed, which is more advantageous.

Due to a problem in drawing, FIG. 3 is drawn such that the axis of the sample flow is perpendicular to the plane defined by the axes of the two directions of the imaging optics. The method of setting these directions is as already described above. Although the cell passage monitoring is performed by using light that is scattered sideways by a cell, the invention is not limited to such a case.

In the embodiments of FIGS. 1 and 3, fluorescence images are taken. However, scattered light images can be taken by properly selecting the light source and a filter (not shown) and properly setting the illumination intensity and the gain of the image intensifier 12. If the scattered light is sufficiently strong, bright scattered light images can be taken even without using the image intensifier 12.

FIG. 5 shows an embodiment of taking transmission light images. In FIG. 5, reference symbol 3a denotes a light source for transmission light image capturing, and numeral 16 denotes a cell passage monitoring light source that emits light constantly. In this embodiment, the cell passage monitoring light source 16 is provided separately from the light source 3a for transmission light image capturing. Reference numeral 17 denotes a dichroic mirror.

A detector 14 is, for instance, a photodiode or a one-dimensional image sensor (line sensor). Although in this embodiment the detector 14 detects transmission light or forward scattered light, it may detect sideway scattered light.

The light source 16 is a CW emission type light source such as a LD, LED or SLD. Although it is desired that the wavelength of the light source 16 be out of the visible range, no specific limitation is imposed thereon. The light source 3a for transmission light image capturing is a pulsed emission type light source capable of a random trigger operation, such as a pulsed laser or a Xe flash lamp.

With the above configuration, the light emitted from the cell passage monitoring light source 16 is reflected by the dichroic mirror 17, and applied to the cell passage monitoring area 44 of the sample flow in the flow cell 1. When it is detected by the detector 14 and the signal processing unit 15 that a cell to be imaged has entered the image capturing area 43, the light source 3a for transmission light image capturing is triggered and emits light. The illumination light passes through the dichroic mirror 17, and illuminates the cell in the flow cell 1.

Transmission light beams carrying images of the cell travel along the same paths as described in connection with FIG. 1, and reach the image capturing unit 10. That is, two transmission light images obtained from the two directions of different angles are formed on the photodetecting surface of the image capturing unit 10, so that two transmission light images are captured for a single cell. Due to a problem in drawing, FIG. 5 is drawn such that the axis of the sample flow is perpendicular to the plane defined by the axes of the two directions of the imaging optics. The method of setting these directions is as already described above.

For example, in the case of measuring a white blood cell, it is difficult for the conventional IFCM to judge whether a neutrophil is a segmented form or a band form. In contrast, the above apparatus enables such discrimination.

The embodiments described above in connection with FIGS. 1, 3 and 5 can be modified in the following manner.

The flow cell 1 may be either a planar sheathed flow cell having a rectangular or elliptical cross-section, or an ordinary circular sheathed flow cell having a circular cross-section. The light source 3a for transmission light image capturing may be either of a pulsed emission type or of a CW emission type.

Where a CW emission type light source is used, the image intensifier 12 having the gating function is disposed before the image capturing unit 10. Where the light source 3a is a CW emission type laser and the image intensifier 12 having a high-speed gating function is used, the cost can be suppressed because a very expensive pulsed laser is not used. The excitation scheme may be either the back illumination scheme or the side illumination scheme.

The cell passage monitoring system may or may not be employed. Where the cell passage monitoring system is employed, the cell passage monitoring light source may also serve as the exciting light source or the light source for transmission light image capturing, or may be provided separately therefrom.

Embodiment 2

Figure 6:
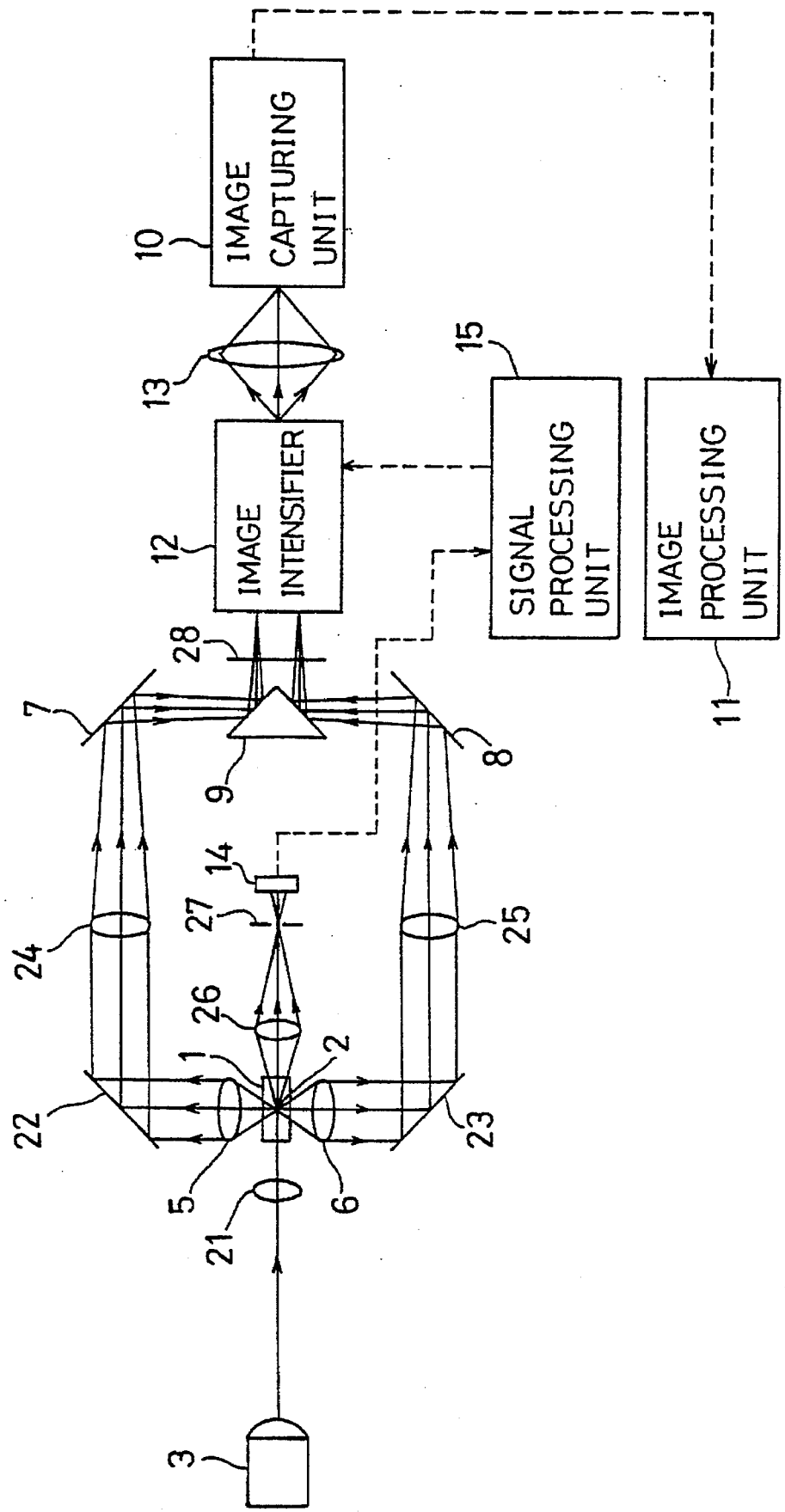
FIG. 6 shows a configuration of an imaging flow cytometer according to Embodiment 2 of the invention.

FIG. 6 shows a configuration of an imaging flow cytometer according to Embodiment 2 of the invention. The same components as in Embodiment 1 are given the same reference numerals and descriptions therefor will be omitted. This embodiment is characterized in that two fluorescence images are captured for a single cell simultaneously with different focal positions.

In FIG. 6, reference numeral 21 denotes a condenser lens; 22, a fourth mirror; 23, a fifth mirror; 24, a first image-forming lens; 25, a second image-forming lens; 26, a collector lens; 27, a pinhole; and 28, a filter that is inserted before the image intensifier 12. The pinhole 27 is provided to receive only light scattered by a cell, i.e., to reduce, to a minimum level, light that is received after being reflected or refracted by the glass wall of the flow cell 1. The filter 28, which should have characteristics that match the wavelength of fluorescence emitted from a cell, serves to eliminate light scattered sideways by a cell or stray light of laser light.

The flow cell 1 is a planar sheathed flow cell. In FIG. 6, the sample liquid 2 flows in the direction perpendicular to the paper surface. The image intensifier 12 has a gating function (optical shutter function).

In this embodiment, the two imaging optics are disposed in directions of ±90° with respect to the optical axis of laser light emitted from the exciting light source 3, and serve to capture two fluorescence images simultaneously. Focal positions for a cell of the respective imaging optics are slightly deviated from each other as shown in FIG. 7.

Figure 7:
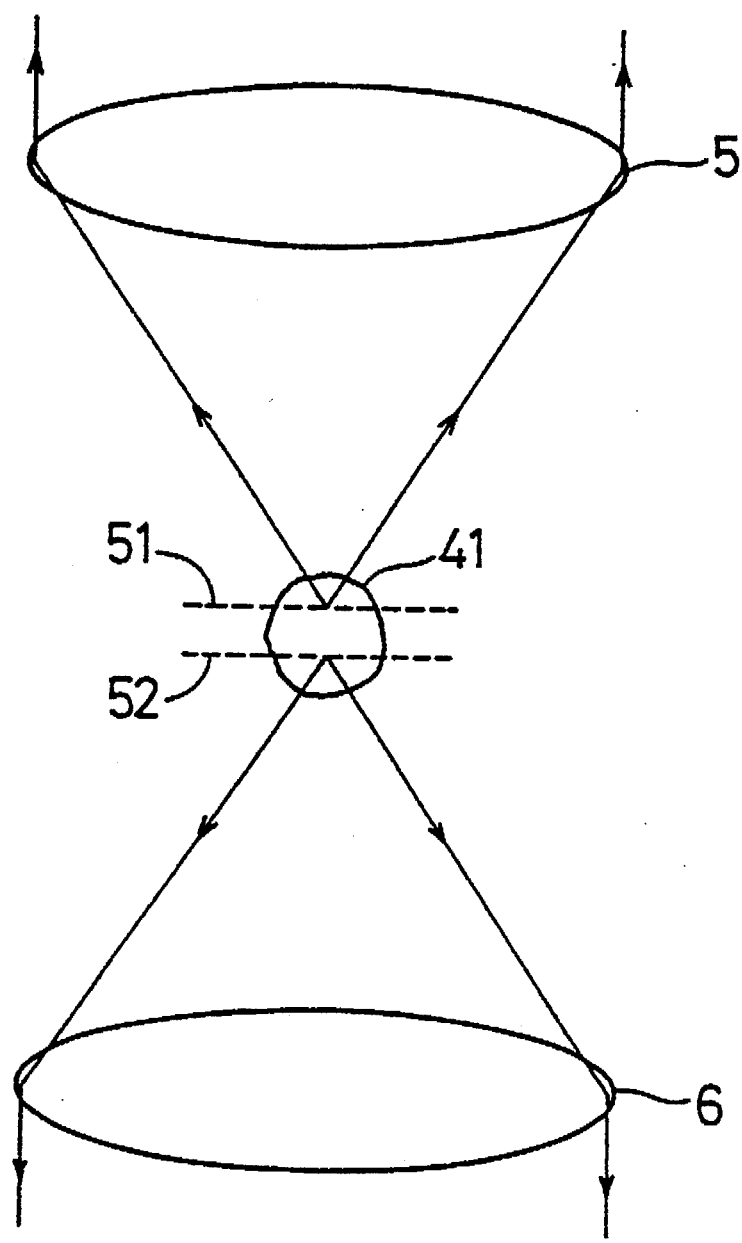
FIG. 7 shows focal positions in the case where two fluorescence images are captured simultaneously by use of two imaging optics.

Referring to FIG. 7, reference numerals 51 and 52 denote focal positions of the first objective lens 5 and the second objective lens 6, respectively. By obtaining two fluorescence images of a single cell with different focal positions in the above manner, minute light emitting portions in a cell can be captured more positively even where the imaging magnification is large and the depth of field is small.

For example, where a cell to be imaged is a blood cell, it is somewhat thicker than 10 μm in the optical axis direction. When it is intended to observe a cell of this size on the screen, the objective lenses 5 and 6 should have a magnification of 60 or more to image it with sufficiently high resolution in two dimensions. Where the image capturing unit 10 is constituted of, for instance, a video camera, the magnification depends on the size of a CCD that forms the photodetecting surface. The depth of field is calculated as about 1.5 μm in this case.

Therefore, when such a large white blood cell is imaged with a single imaging optics, a resulting fluorescent image will be such that focusing is made only in a region including a focal plane which region is thin in the optical axis direction. Therefore, if a cell has a complex shape in the optical axis direction, portions away from the focal plane cannot be observed or result in a blurred image. This is a serious problem when the imaging flow cytometer having the fluorescence image capturing function is applied to such a measurement as FISH. For example, FISH measures the number of light emitting points in the nucleus of a cell. If light emitting points are distributed in a plane perpendicular to the optical axis and focusing is made on that plane, all the light emitting points can be observed. However, if light emitting points are distributed in the optical axis direction, light emitting points on the focused plane can be observed, however light emitting points away from that plane cannot be observed or are observed as large blurred light emitting points. Thus, light emitting points cannot be observed correctly, disabling their counting.

To solve this problem, two images with focal positions that are slightly deviated from each other are captured. In this embodiment, the two imaging optics are disposed in the directions of ±90°, and two fluorescence images are captured using those two imaging optics simultaneously with focal positions that are slightly deviated from each other. With this configuration, all the light emitting points can be imaged which are distributed three-dimensionally in a cell.

In this embodiment, since the flow cell 1 is a planar sheathed flow cell, narrowed laser light can be applied to the sample flow in its narrow-side direction as shown in FIGS. 4(a) and 4(b). Therefore, the intensity of the excitation light for causing fluorescence can be increased, to enable production of fluorescence images having large S/N ratios.

With the above configuration, fluorescence beams emitted in the directions of ±90° with respect to the optical axis of laser light emitted from the exciting light source 3 are collected by the first and second objective lenses 5 and 6, and then reflected by the fourth and fifth mirrors 22 and 23, respectively. One fluorescence is imaged on one side of the input surface of the image intensifier 12 via the first image-forming lens 24, first mirror 7 and third mirror 9. The other fluorescence is imaged on the other side of the input surface of the image intensifier 12 via the second image-forming lens 25, second mirror 8 and third mirror 9.

Faint fluorescence images formed on the input surface of the image intensifier 12 are amplified by a factor of several thousand to several tens of thousand and then appear on its output surface. The output images are taken by the image capturing unit 10 via the relay lens 13. Thus, brighter fluorescence images are obtained.

In the above manner, all the light emitting points are captured which are distributed three-dimensionally in a cell.

As described above, the image intensifier 12 having the gating function is employed to produce fluorescence images of a moving cell without causing a blur. The image intensifier 12 is controlled so that the gate is opened only instantly when a cell reaches the laser light illumination area.

Although the image intensifier 12 having the gating function is employed in this embodiment, it is possible as described below to produce fluorescence images without causing a blur by employing a pulsed emission type light source such as a pulsed laser or a xenon lamp without using a gate or even without using an image intensifier.

To positively capture images of a cell or a microorganism entering the excitation light illumination area (image capturing area), the cell passage monitoring system detects, by the detector 14, the light applied from the light source 3 to the sample flow 2 and then scattered by a cell or a microorganism, and opens the gate of the image intensifier 12 based on the detection signal. That is, forward scattered light of the laser light (excitation light) emitted from the light source 3 is collected by the collector lens 26, and detected by the detector 14 via the pinhole 27. Light reflected or refracted by the glass wall etc. of the flow cell 1 is eliminated by the pinhole 27, so that only the light scattered by a cell is received by the detector 14. The detection signal is sent to the signal processing unit 15, which generates a control signal for opening the gate of the image intensifier 12.

Figure 8:
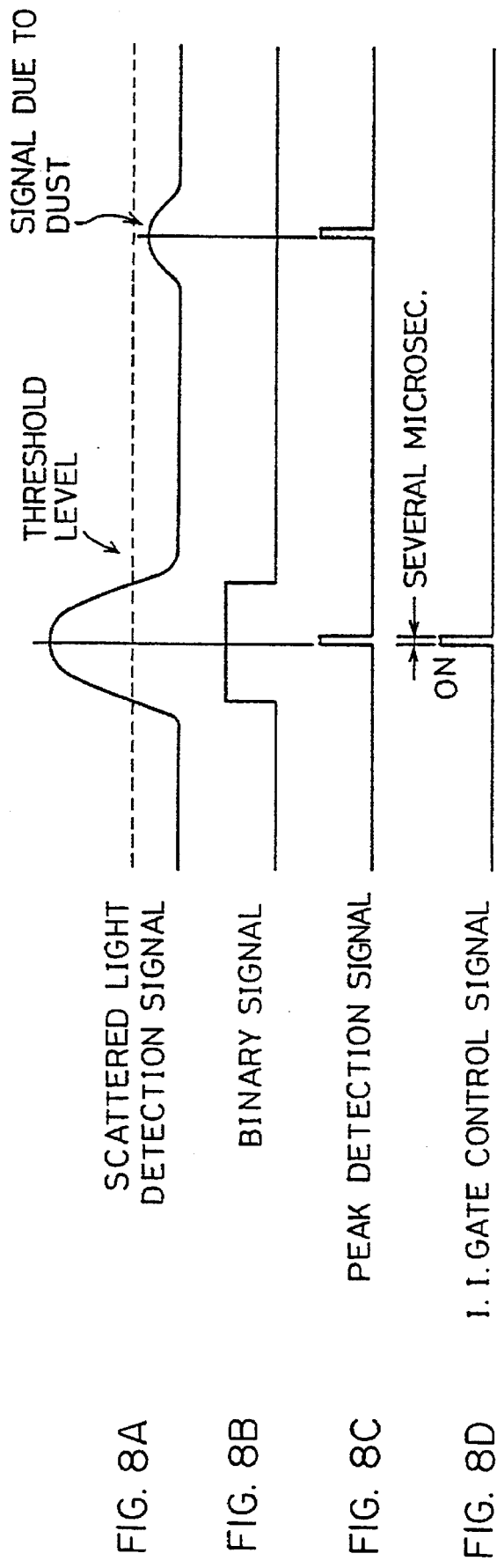
FIG. 8 shows an example of a scattered light detection signal of a detector.

FIG. 8 shows an example of the scattered light detection signal of the detector 14. The processing of the signal processing unit 15 allows only the effective cells to be imaged selectively. Minute dust or cell fragments are smaller and cause weaker scattered light intensity than cells or blood cells to be imaged. Utilizing this fact, the judgment as to whether a subject cell has reached the image capturing area can be made based on the magnitude of the scattered light detection signal.

Specifically, as shown in FIG. 8, a comparison is made to judge whether the amplitude of the scattered light detection signal is larger than a prescribed threshold level, to thereby produce a binary signal. On the other hand, it is necessary to open the gate of the image intensifier 12 when a cell or a microorganism is just located in the excitation light illumination area. To this end, the peak of the scattered light detection signal is detected to produce a peak detection signal.

An I.I. gate control signal for opening the gate of the image intensifier 12 is generated based on the peak detection signal and the binary signal. The period of opening the gate of the image intensifier 12 should be set short to obtain fluorescence images that are free of a blur. For example, when the flow speed of the sample flow is 100 mm/sec, control is so made as to open the gate for several microseconds.

Figure 9:
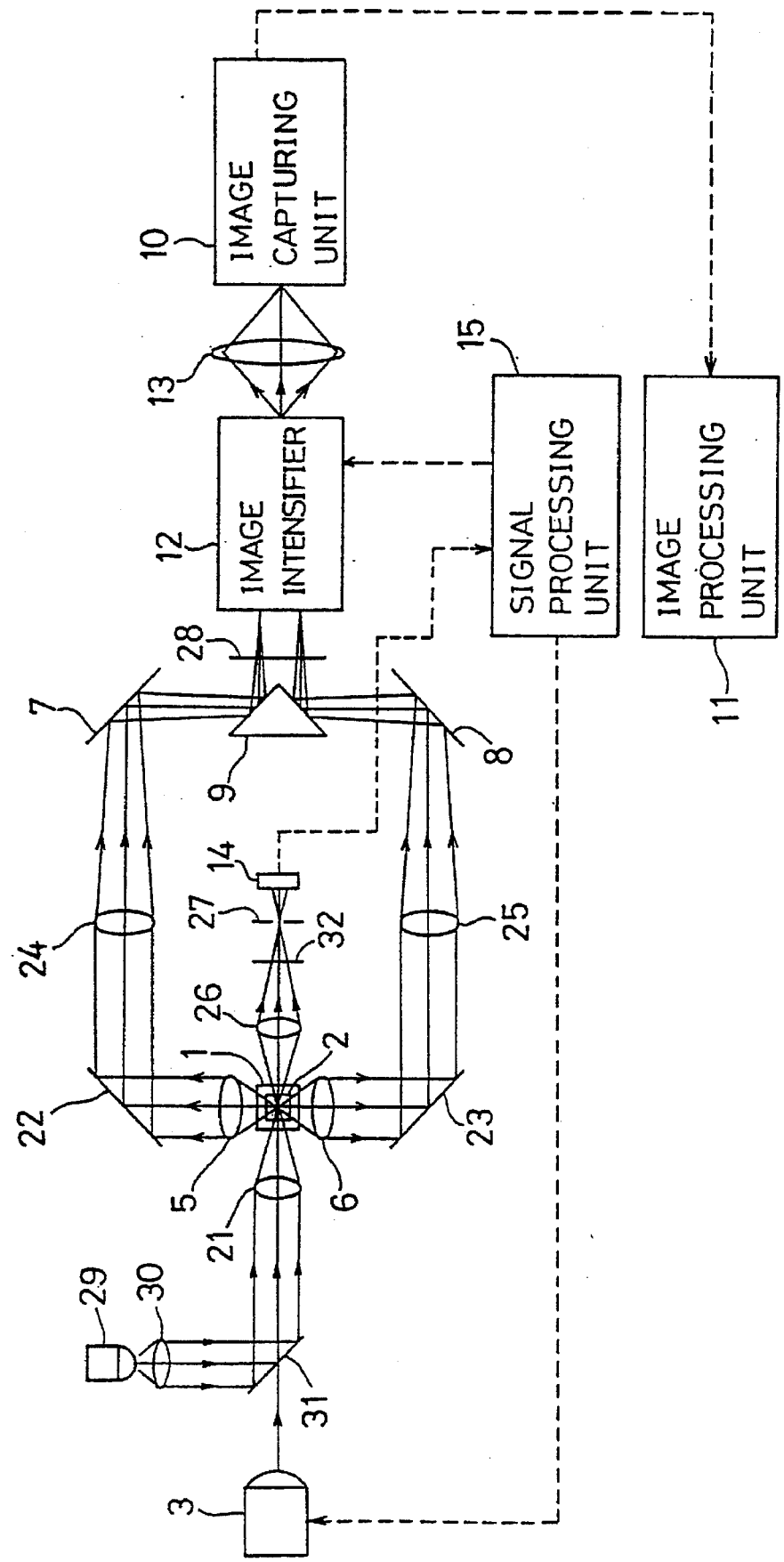
FIG. 9 shows an embodiment in which an exciting light source is of a pulsed emission type.

FIG. 9 shows an embodiment in which the exciting light source 3 is of a pulsed emission type. In FIG. 9, reference numeral 29 denotes a cell passage monitoring light source of a CW emission type; 30, a collimator lens; 31, a dichroic mirror; 32, a filter for cutting light emitted from the pulsed emission type light source 3.

For example, the pulsed emission type light source 3 is a pulsed laser or a xenon flash lamp. Since, in general, the pulsed laser can emit high-intensity light during a very short period of less than several nanoseconds, it enables production of images that are free of a blur even if the flow speed of the sample flow is as fast as several meters per second. In this case, the amount of analyses per unit time can be made large even if the sample flow is not flat. In some cases, fluorescence images can be obtained with an ordinary video camera without using the image intensifier 12 for amplifying fluorescence.

This embodiment is provided with the cell passage monitoring system. Since the exciting light source 3 is of a pulsed emission type, the CW emission type light source 29 for cell passage monitoring is separately provided to detect light scattered by a cell. For example, the CW emission type light source 29 may be a semiconductor laser for emitting near infrared light.

With the above configuration, light emitted from the cell passage monitoring light source 29 is converted to parallel light by the collimator lens 30, reflected by the dichroic mirror 31, narrowed by the condenser lens 21, and finally applied to the sample flow flowing through the flow cell 1.

Light scattered by a cell is collected by the collector lens 26, passes through the filter 32, and received by the detector 14 via the pinhole 27.

The scattered light detection signal output from the detector 14 is subjected to the signal processing in the signal processing unit 15 as in the case of the FIG. 6 embodiment. When a subject cell has just reached the image capturing area, the signal processing unit 15 supplies the pulsed emission type light source 3 with a trigger signal for causing the light source 3 to emit light.

When the pulsed emission type light source 3 applies light to the flow cell 1, two fluorescence images are formed on the photodetecting surface of the single image capturing unit 10 by the two imaging optics that are disposed in directions of ±90° with respect to the optical axis of the light source 3.

The fluorescence images taken by the image capturing unit 10 are sent, as a video signal, to the image processing unit 11, which performs various image processing on the obtained fluorescence images.

Although the image intensifier 12 is used in this embodiment, fluorescence images may be captured without it if fluorescence emitted from a cell is sufficiently strong. Where the light source 3 is of a pulsed emission type, the image intensifier 12 not having a gating function can be used.

FIG. 10 shows an example of a fluorescence imaging screen, which was obtained when a fluorescence-marked DNA probe was hybridized with chromosomes, to perform a test for abnormality in the number of chromosomes.

In this example of the imaging screen, the left-hand half is a fluorescence image taken along the direction of +90° with respect to the optical axis via the objective lens 5, and the right-hand half is a fluorescence image along the direction of –90° with respect to the optical axis via the objective lens 6. The two images were taken simultaneously with the single image capturing device, i.e., a combination of the image intensifier 12 and the image capturing unit 10.

In the left-hand image, fluorescence emitting portions are found at a top-right position and a top-right position of the nucleus. On the other hand, in the right-hand image, while the top-left light emitting portion is not found, another fluorescence emitting portion is found at a bottom position of the nucleus. In this example, only two fluorescence emitting portions can be recognized from each of the left-hand and right-hand fluorescence images. However, by properly processing the left-hand and right-hand fluorescence images, the existence of a total of three fluorescence emitting portions in the nucleus can be recognized in which the top-left light emitting portion in the left-hand image and the top-right light emitting portion in the right-hand image are regarded as the same light emitting portion.

Embodiment 3

Figure 11:
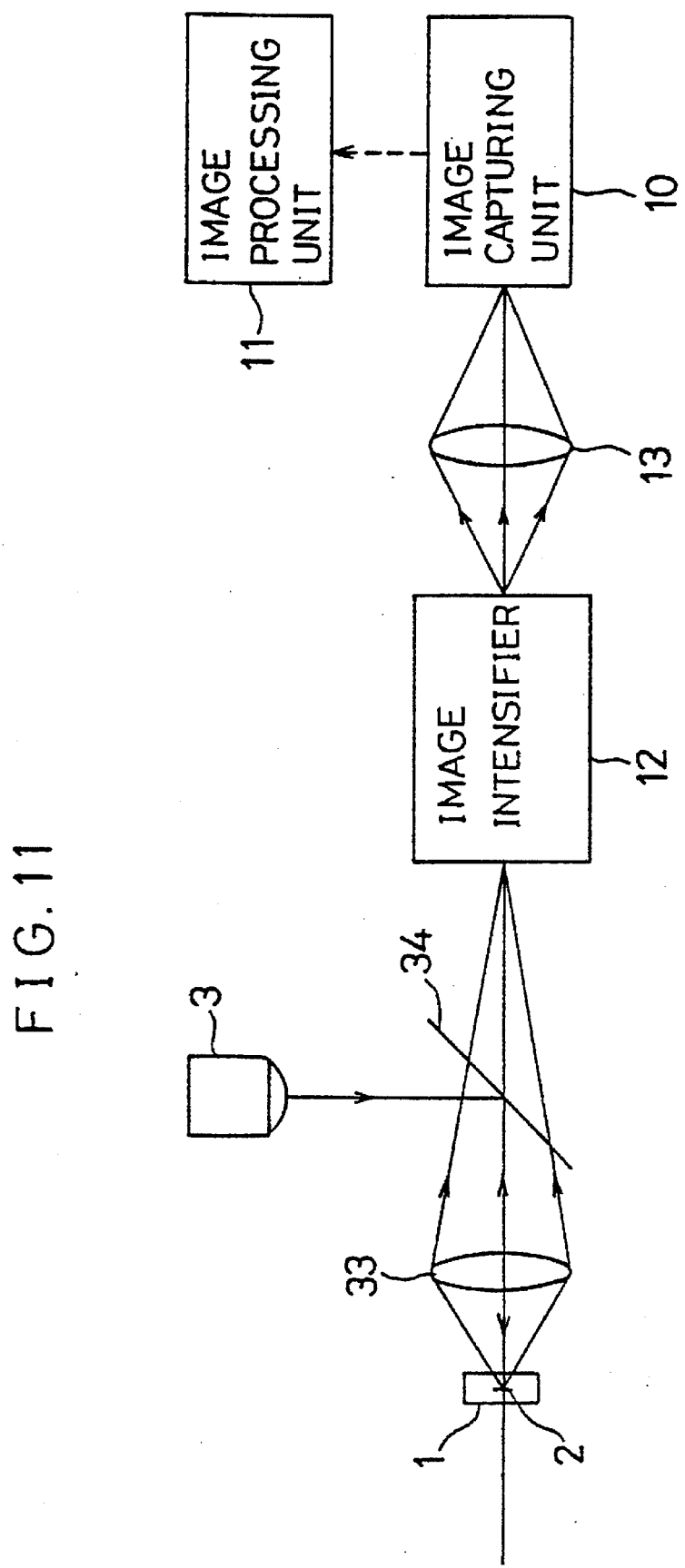
FIG. 11 shows a configuration of an imaging flow cytometer according to Embodiment 3 of the invention.

FIG. 11 shows an imaging flow cytometer according to Embodiment 3 of the invention. The see components as in Embodiments 1 and 2 are given the same reference numerals and descriptions therefor will be omitted. This embodiment is characterized in that a plurality of fluorescence images are captured for a single cell at different time points with different focal positions.

In FIG. 11, reference numerals 33 and 34 denote an objective lens and a dichroic mirror, respectively. In FIG. 11, the sample liquid 2 flows in the direction perpendicular to the paper surface. The exciting light source 3 is a CW emission type laser light source such as an Ar laser. Light emitted from the light source 3 is reflected by the dichroic mirror 34, and then applied to the sample flow in the back illumination scheme.

The image intensifier 12 having the gating function is employed, and its gate is caused to operate periodically. The gate operating period of the image intensifier 12, which varies with the flow speed of the sample flow, is set at such a period that fluorescence images are not blurred and are as bright as possible. For example, when the flow speed of the sample flow is 100 mm/sec, the gate opening period is set at about 3 μsec.

If a fluorescence-dyed cell exists in the image capturing area of the flow cell 1 while the image intensifier 12 is operating, a fluorescent substance contained in the cell is excited, and very faint fluorescence emitted from the substance is amplified by the image intensifier 12 by a factor of several tens of thousand and taken by the image capturing unit 10 via the relay lens 13. Where the image capturing unit 10 is, for instance, a video camera, the operation of the image intensifier 12 is usually synchronized with the video rate of the camera, i.e., 30 times/sec.

Figure 12:
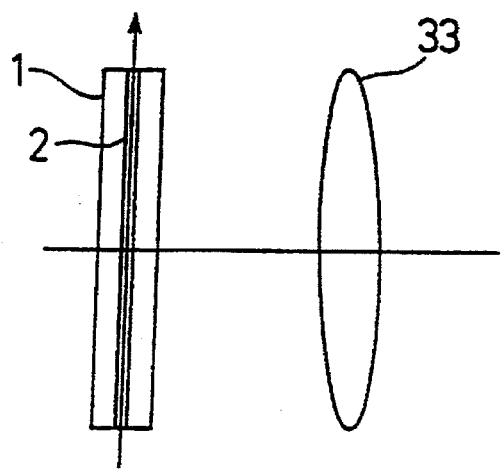
FIGS. 12(a) and 12(b) are side views showing configurations of a flow cell and its periphery.
Figure 12:
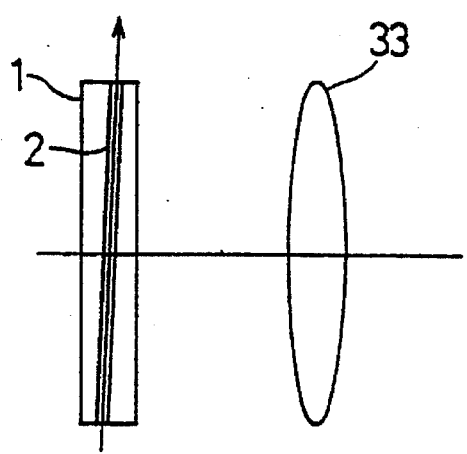

FIGS. 12(a) and 12(b) are side views showing configurations of the flow cell and its periphery. In these drawings, the sample flow flows in the top-bottom direction on the paper surface.

The ordinary imaging flow cytometer employs a planar flow cell, in which the flow path of the sample flow is set perpendicular to the optical axis. This arrangement is employed so that focusing is made on the same portion of cells even if they pass through different positions of the image capturing area.

In this embodiment, setting so made that the sample flow (i.e., the flow of the sample liquid 2) is inclined in the plane including the sample flow and the optical axis, that is, the sample flow is inclined from the focal plane of the objective lens 33. To realize such an arrangement, the flow cell 1 itself may be inclined as shown in FIG. 12(a), or the flow cell 1 may be so manufactured that the sample flow is inclined with respect to the flow cell 1 as shown in FIG. 12(b).

With the above configuration, as a cell moves through the flow cell 1 along the sample flow, its position relative to the focal plane of the objective lens 33 (i.e., the distance from the objective lens 33) is varied. Therefore, by imaging, plural times at different time points, a cell that moves so as to cross the focal plane of the objective lens 33, images with different focused positions with respect to the single cell can be obtained.

If a cell is imaged in the above manner with the gate of the image intensifier 12 opened for a long period, resulting images will be elongated. To avoid such a case, where the image capturing unit 10 uses a video camera, the image intensifier having a high-speed gating function is employed and the gate is opened several times during a one-frame period of the video camera. As a result, several cell images with different focused positions can be produced in one frame.

With the above configuration, the deviations between focused positions can be changed relatively easily by changing only the mounting angle of the flow cell 1.

Figure 13:
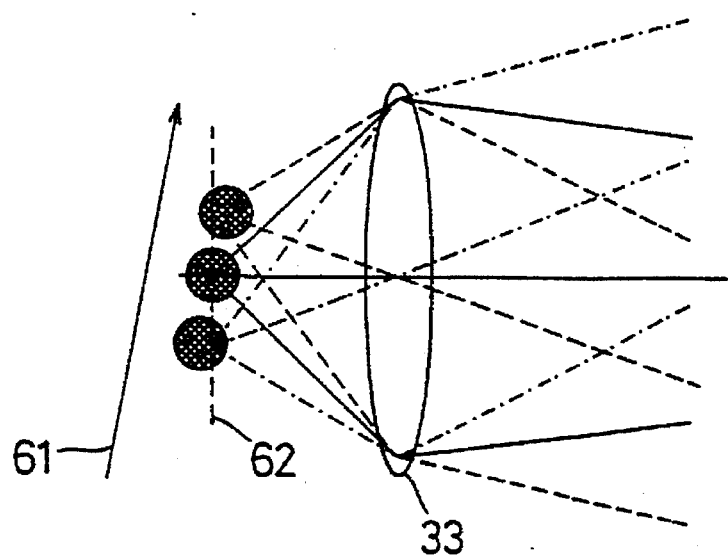
FIG. 13 is an enlarged view showing a portion where a cell is imaged.

FIG. 13 is an enlarged view showing a portion where a cell is imaged. In FIG. 13, reference numerals 61 and 62 denote a direction of the sample flow and a focal plane of the objective lens 33, respectively. As shown in FIG. 13, a plurality of fluorescence images are obtained for a single cell with different focused positions.

FIGS. 14(a) and 14(b) show examples of imaging screens, which are fluorescence imaging screens obtained when a DNA probe subjected to a FISH treatment, i.e., fluorescence marking was hybridized with chromosomes, to perform a test for abnormality in the number of chromosomes. A white blood cell having three light emitting points was measured.

FIG. 14(a) is an example of an image obtained by causing the image intensifier 12 to operate three time while the cell exists in the image capturing area. FIG. 14(b) is an example of an image obtained by the conventional imaging flow cytometer.

In the conventional example of FIG. 14(b), two light emitting points (located at a top-right position) of the three light emitting points are located on each other in the optical axis direction. When a measurement is conducted using the conventional imaging flow cytometer, while a light emitting point existing in a focused plane is observed clearly, a light emitting point not existing in the focused plane is very blurred and observed as an image of low emission intensity. Two light emitting points located on each other are observed as a single light emitting point, in this example, as a single blurred light emitting point.

In contrast, in the image of FIG. 14(a) according to this embodiment, all the light emitting points are clear, and even light emitting points that are located on each other in the optical axis direction can be recognized as separate light emitting points because they can be observed clearly by virtue of the use of different focused planes. That is, according to this embodiment, several images are taken for a single cell by use of different focused planes, and sent to the image processing unit 11 as a single image. The image processing unit 11 performs various image processing on the obtained fluorescence images.

The inclination angle of the sample flow is determined from the depth of field, the cell size, and other factors. The interval of causing the gate of the image intensifier 12 to operate is determined from the flow speed etc. The illumination light of the exciting light source 3 should be applied to the entire image capturing area uniformly.

Although fluorescence images are taken in this embodiment, the invention is not limited to such a case. Scattered light images can be captured by replacing the dichroic mirror 34 of FIG. 11 with a beam splitter. In this case, since scattered light is stronger than fluorescence, the storage time can be shortened by reducing the operating period of the image intensifier 12. Since the flow speed of the sample flow can be made faster, the amount of analyses per unit time can be increased.

Although in this embodiment the exciting light source 3 of a CW emission type and the image intensifier 12 having a high-speed gating function are used, the exciting light source 3 of a pulsed emission type, such as a semiconductor-pumped solid-state pulsed laser, having a repetition frequency of more than several thousand pps (pulses per second) and the image intensifier 12 having an ordinary gating function (not a high-speed type) may be used. Where a pulsed emission type light source having very high output energy is used, fluorescence images can be taken without using the image intensifier 12.

Figure 15:
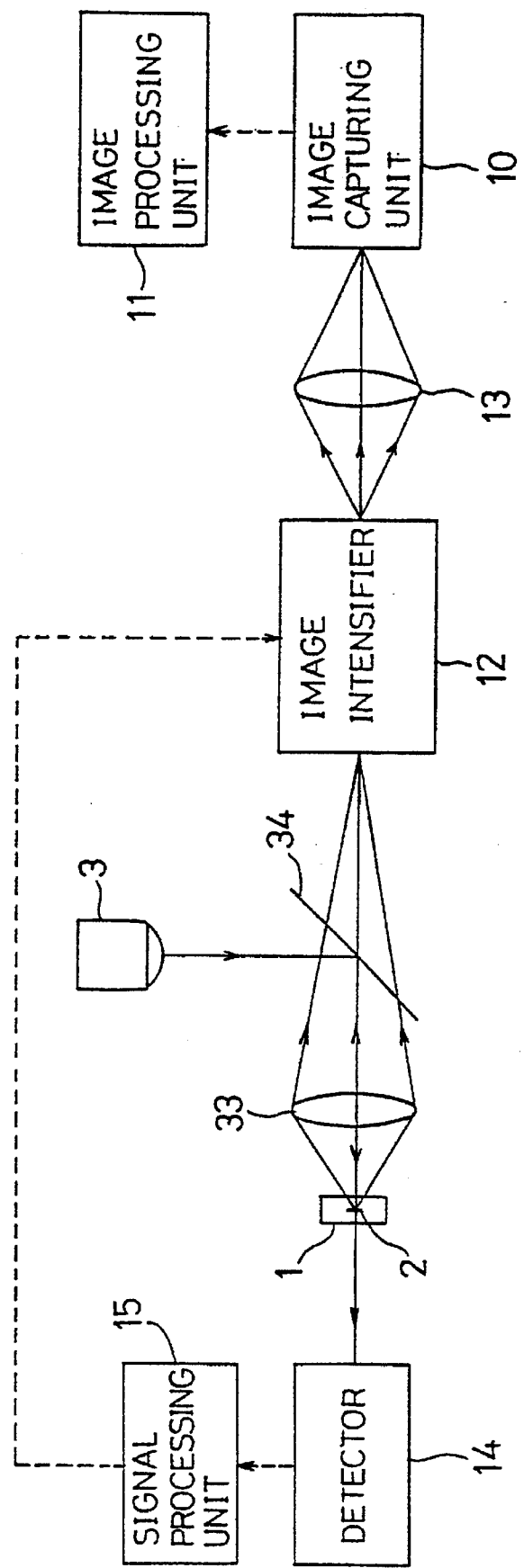
FIG. 15 shows an embodiment in which a cell passage monitoring system is added.

FIG. 15 shows an embodiment in which the cell passage monitoring system is added. In the embodiment of FIG. 11, the gate of the image intensifier 12 is caused to operate periodically. However, where the density of cells is low, the probability that a cell just exists in the image capturing area when the image intensifier 12 operates is low. Thus, the imaging efficiency is also low. Further, since imaging positions are not fixed, even if the image intensifier 12 operates three times (for example), the number of images, which should be three, may be two or less in some cases. To solve this problem, the cell passage monitoring function is added as in this embodiment.

In this embodiment, the exciting light source 3 also serves as the cell passage monitoring light source. The cell passage monitoring is performed using forward scattered light or transmission light. Alternatively, the cell passage monitoring may be performed using sideway scattered light. The cell passage monitoring detector 14 is a photodiode, a line sensor, or the like.

Figure 16:
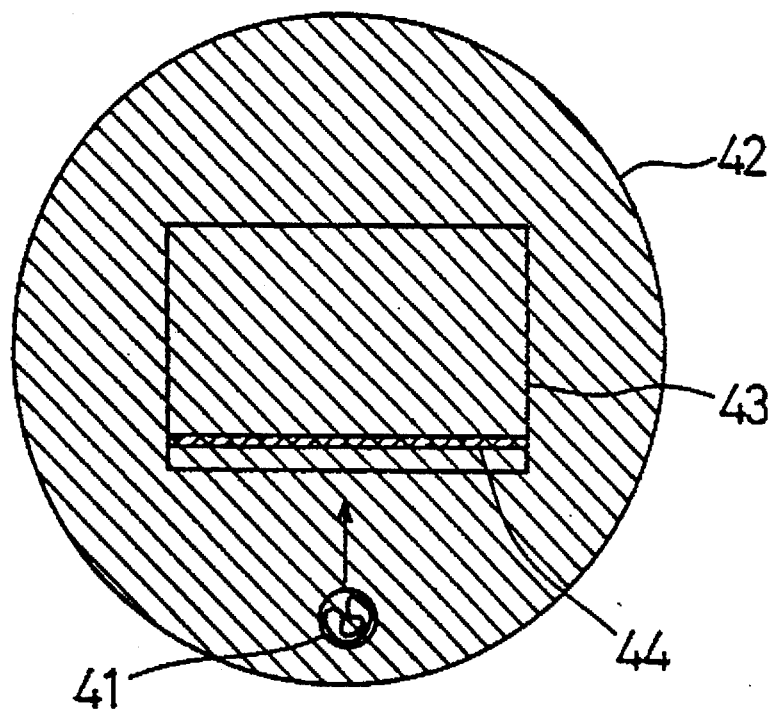
FIG. 16 shows a relationship between a cell passage monitoring area and an image capturing area.

FIG. 16 shows a relationship between the cell passage monitoring area and the image capturing area. As shown in FIG. 16, a cell passage monitoring area 44 is a long and narrow rectangle, is perpendicular to the flow of the sample liquid 2, and has a width approximately equal to or longer than the width of an image capturing area 43. The cell passage monitoring area 44 is provided at an upstream position in the sample flow of the image capturing area 43. This arrangement is practical, though the cell passage monitoring area 44 may be provided at the center of the image capturing area 43.

Where the detector 14 is a photodiode, a slit is used to monitor the cell passage monitoring area 44. Where the detector 14 is a line sensor, the line sensor is so disposed that its monitoring area coincides with the cell passage monitoring area 44.

A signal produced from the detector 14 is sent to the signal processing unit 15, which generates trigger signals to cause the image intensifier 12 to operate plural times with slight time differences. The signal processing unit 15 can judge the cell size based on the detection signal of the detector 14 indicating the intensity of scattered light, and can perform control so as not to effect imaging if dust or the like, instead of a cell, enters the image capturing area 43.

When the cell passage monitoring system and the signal processing unit 15 detect that a cell has entered the image capturing area, the gate of the image intensifier 12 is opened and the image intensifier 12 operates several times with slight time differences. Thus, a screen including a plurality of fluorescence images for a single cell is obtained as shown in FIG. 14(a).

In this embodiment, the image intensifier 12 is caused to operate several times for imaging. Therefore, the next cell might enter the image capturing area 43 when the image intensifier 12 operates for the last one (or an operation close to the last one) of a series of imaging operations. (This possibility would be very low if the density of cells is low.) In such a case, an image of the next cell will be superimposed on an image taken in the first imaging operation (or an operation close to the first).

Where the cell passage monitoring system is not used, there is no other way of judging for overlapping of cells than based on the obtained images. However, where the cell passage monitoring system is used, the cell passage monitoring system can judge for overlapping of cells. A specific example will be described below.

First, a description will be made of a case where the detector 14 of the cell passage monitoring system is a photodiode.

It is assumed that the flow speed of the sample flow is 100 mm/sec and the image intensifier 12 operates three times for a single cell. It is further assumed that the operating period of the image intensifier 12 is 5 μsec and its operating interval is 250 μsec.

Since the detector 14 is a photodiode, a slit is provided to restrict the cell passage monitoring area 44 to part of the image capturing area 43. When a signal indicating cell passage is supplied from the detector 14 to the signal processing unit 15, the signal processing unit 15 produces a trigger signal for causing the image intensifier 12 to operate.

It is assumed that imaging operations are performed in a certain imaging frame. If passage of the next cell is detected before completion of the third (i.e., last) operation of the image intensifier 12 in that frame period, there is a possibility that an image of a later detected cell is superimposed on an image taken first. Therefore, images taken in this frame are made ineffective. That is, where the cell passage monitoring is performed using a photodiode, it can be detected that the next cell has entered the image capturing area while the current cell is imaged. In such a case, images of both cells are made ineffective.

Figure 17:
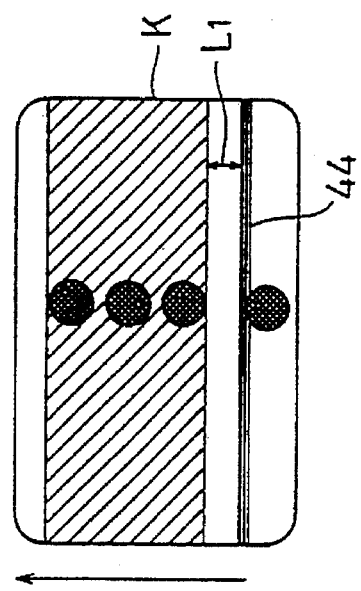
FIGS. 17(a) and 17(b) show an example of detecting overlapping of cells in the case where a photodiode is used.
Figure 17:
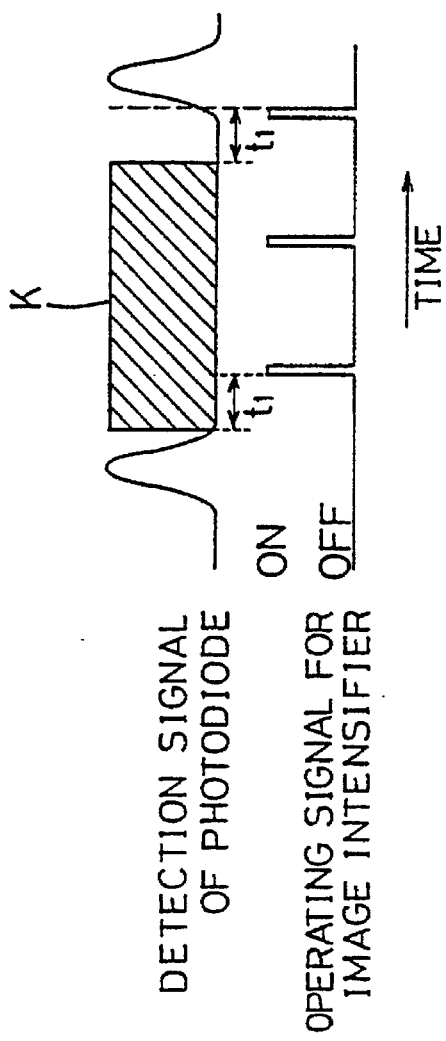

FIGS. 17(a) and 17(b) show an example of detecting overlapping of cells in the case where a photodiode is used. More specifically, FIGS. 17(a) shows a detection signal of the photodiode and operating signals for the image intensifier 12, and FIG. 17(b) shows an example of a screen obtained with the detection signal of FIG. 17(a).

In FIG. 17(a), when cell passage is detected by the detection signal of the photodiode, operating signals are sent to the image intensifier 12, which operates three times, for instance. If no cell passage is detected during a prohibited region K shown in FIGS. 17(a) and 17(b), three produced fluorescence images are effective. For example, when cell passage is detected at a timing that is out of the prohibited region K, there will occur no overlapping even if a cell flows along the same path as the previous cell. Therefore, only the three cell images are cut out by image processing and made effective.

In FIG. 17(b), $L_1$ is expressed as $$L_1 = v \cdot t_1,$$

where v is cell flow speed. In this embodiment, the prohibited region K is made narrow to increase the number of effective cells as much as possible. The apparatus can be so constructed as to always display only the effective cell on the screen, by changing the cell passage monitoring position and the area of the prohibited region K. The width of the prohibited region K is determined from the cell flow speed, the operation timings of the image intensifier 12, and other factors.

Next, a description will be made of a case where the detector 14 of the cell passage monitoring system is a line sensor. It is assumed that the imaging conditions are the same as the above case. Where the detector 14 is a line sensor, not only the cell size but also the cell passage position in the image capturing area 43 can be detected.

Even when passage of the next cell is detected before completion of the third (i.e., final) operation of the image intensifier 12 in a certain frame period, images taken first can be made effective and the next cell can be made ineffective if it is confirmed that the positions of the cell coming first and the cell coming next are not overlapped with each other. If there is only a slight overlap between the positions of the two cells, images of both cells are made ineffective.

Figure 18:
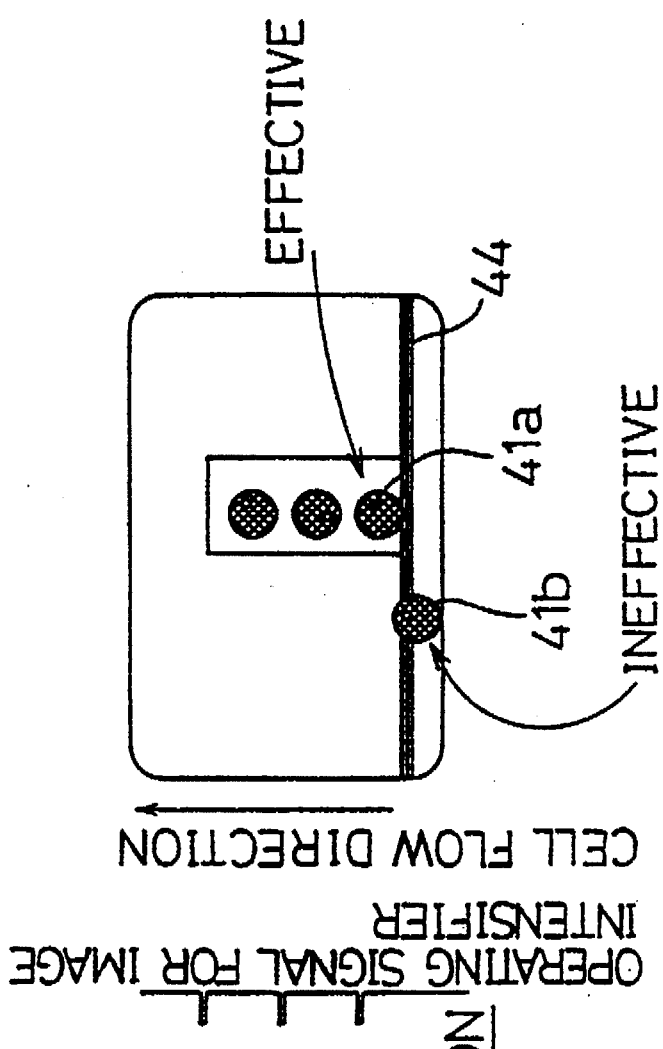
FIGS. 18(a) and 18(b) show an example of detecting overlapping of cells in the case where a line sensor is used.
Figures 19A, 19B:
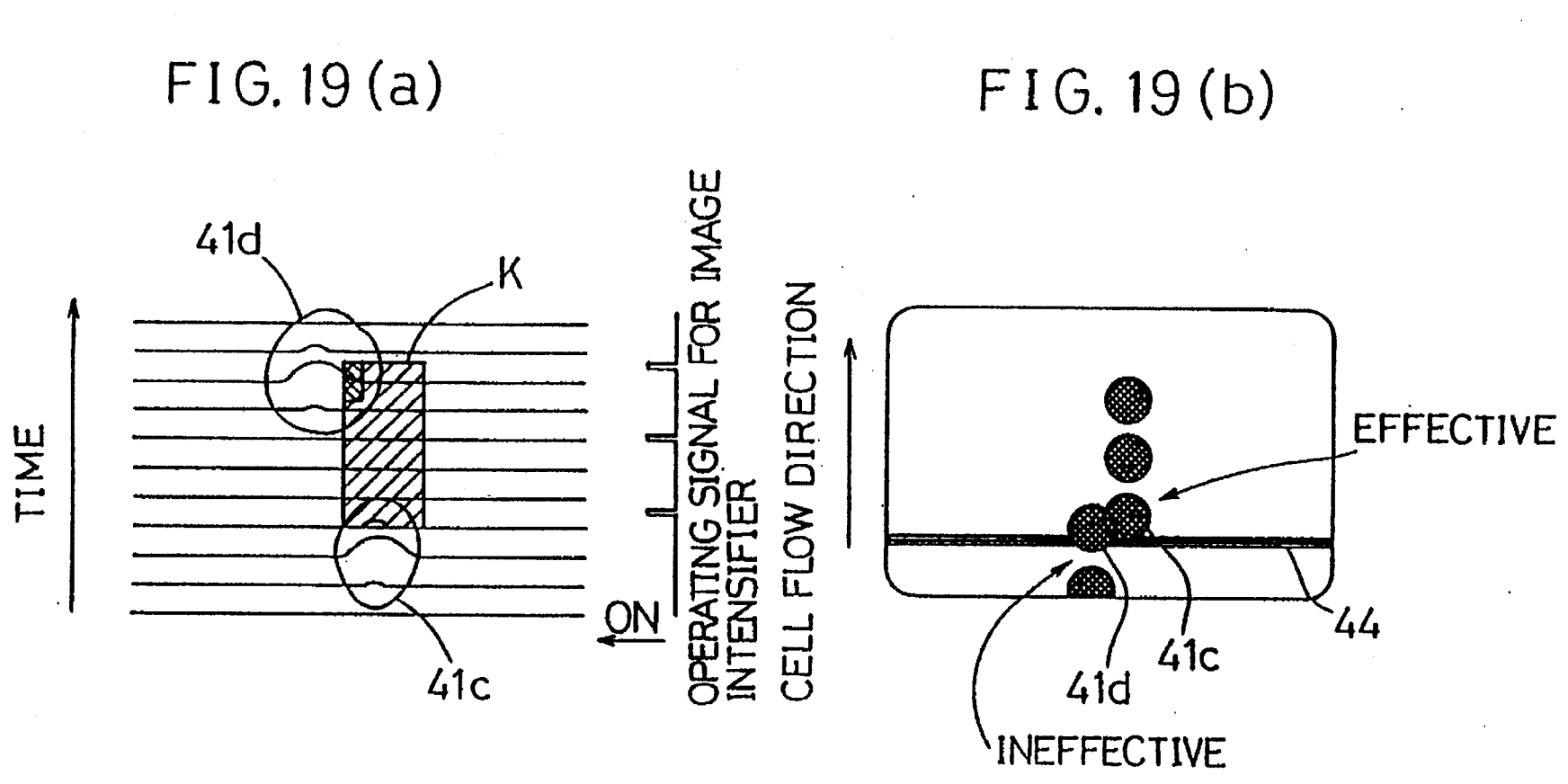

FIGS. 18(a)–18(b) and 19(a)–19(b) show examples of detecting overlapping of cells in the case where a line sensor is used. More specifically, FIG. 18(a) shows detection signals of the line sensor and operating signals for the image intensifier 12, and FIG. 18(b) shows an example of a screen obtained with the detection signals of FIG. 17(a). Similarly, FIG. 19(a) shows detection signals of the line sensor and operating signals for the image intensifier 12, and FIG. 19(b) shows an example of a screen obtained with the detection signals of FIG. 19(a).

In the example of FIGS. 18(a) and 18(b), although the next cell 41b enters the image capturing area during the third operation of the image intensifier 12, images of the first cell 41a are made effective and an image of the next cell 41b is made ineffective because the positions of the two cells are not overlapped with each other.

In the example of FIGS. 19(a) and 19(b), the flowing position of the next cell 41d overlaps with the position of the first cell 41c, images of both cells are made ineffective.

Figure 20:
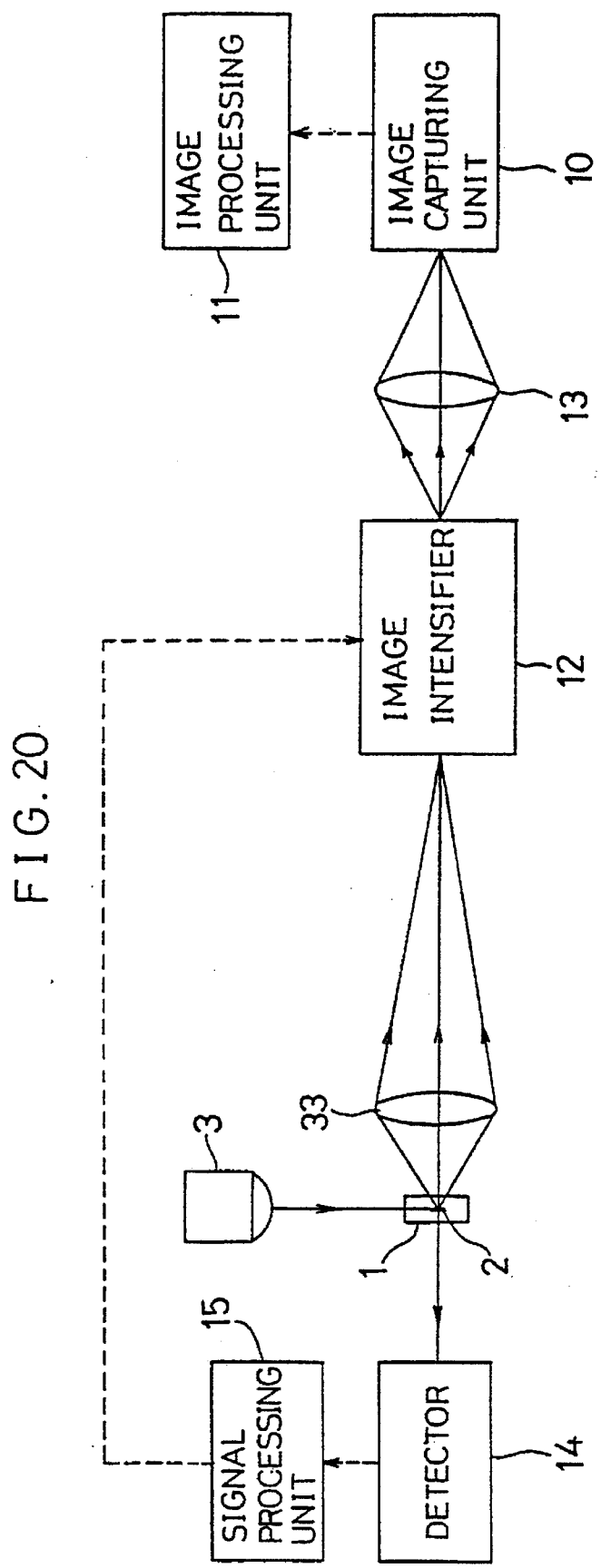
FIG. 20 shows an embodiment in which excitation light is applied from the side of a flow cell.

FIG. 20 shows an apparatus of an embodiment which employs the scheme (side incidence scheme) of applying the excitation light from the side of the flow cell 1. Where the excitation light is applied according to the back illumination scheme, it is necessary to increase the illumination area of the excitation light to a great extent, to apply the excitation light uniformly over the entire image capturing area. Therefore, the laser beam cannot be narrowed much, which is disadvantageous in terms of the illumination intensity per unit area.

To make an improvement in this respect, in this embodiment, the excitation light is applied from the side of the flow cell 1. As shown in FIG. 4(b), the excitation light is applied in an elliptical shape having a major axis that is sufficiently longer than the longitudinal size of the image capturing area and a minor axis that is sufficiently longer than the thickness of cells to be imaged. With this arrangement, the illumination intensity per unit area can be increased from the case of applying the excitation light in the shape shown in FIG. 16. In this embodiment, the cell passage monitoring system is added to perform cell passage monitoring by use of sideway scattered light.

According to the invention, since a plurality of, different images are captured for a single particle, all the minute fluorescence emitting portions that are distributed three-dimensionally can be detected, for instance, in a FISH measurement, in contrast to the conventional apparatus which cannot perform such detection correctly. As a result, the invention assures highly accurate measurements.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An imaging flow cytometer comprising:
   a transparent flow cell, through which a sample liquid containing at least one particle flows;
   light emitting means for emitting a light beam to illuminate the at least one particle in the transparent flow cell; and
   image capturing means for nearly simultaneously capturing a plurality of different images, the plurality of images being captured based on a plurality of light beams nearly simultaneously leaving the particle in a plurality of different directions after the illuminating light beam has interacted upon the at least one particle being located in an image capturing area of the transparent flow cell.

2. The imaging flow cytometer according to claim 1, wherein the image capturing means capture the plurality of different images for the at least one particle nearly simultaneously, each image being captured from a different one of a plurality of focal positions.

3. The imaging flow cytometer of claim 2, wherein the image capturing means includes at least a first and second objective lens, each with different focal positions.

4. The imaging flow cytometer according to claim 1, wherein the light emitting means includes a fluorescence exciting light source for applying fluorescence excitation light to the image capturing area of the flow cell, the image capturing means capturing fluorescence images of the at least one particle located in the image capturing area of the flow cell.

5. The imaging flow cytometer according to claim 4, wherein the fluorescence exciting light source is a pulsed emission type light source.

6. The imaging flow cytometer according to claim 4, wherein the fluorescence exciting light source is a continuous-wave (CW) emission type light source, and the image capturing means includes a gating means for opening and closing an optical path leading to the image capturing means.

7. The imaging flow cytometer according to claim 5 or 6, further comprising a particle passage monitoring system including a monitoring light source for applying light to a flow of the sample liquid in the flow cell, and a detector for detecting light emitted from the at least one particle within the image capturing area of the flow cell.

8. The imaging flow cytometer according to claim 7, wherein the fluorescence exciting light source also serves as the monitoring light source.

9. The imaging flow cytometer according to claim 4, wherein at least one particle contained in the sample liquid has been preprocessed by a reagent that causes fluorescence.

10. The imaging flow cytometer according to claim 4, wherein a flow of the sample liquid in the flow cell is a flat sheath flow, and light emitted from the fluorescence exciting light source is input from a relatively narrower width side of the sheath flow.

11. The imaging flow cytometer according to claim 1, further comprising a particle passage monitoring system including a detector for detecting passage of a particle.

12. An imaging flow cytometer, comprising:
   light emitting means for emitting a light beam to illuminate a transparent flow cell, wherein the transparent flow cell includes a sample liquid containing at least one particle;
   first optical channeling means for optically channeling a first light beam traveling from the transparent flow cell in a first direction in response to the illuminating light beam interacting with the at least one particle;
   second optical channeling means for optically channeling a second light beam traveling from the transparent flow cell in a second direction from the first direction in response to the same illuminating light beam interacting with the at least one particle, the first and second optically channeling means nearly simultaneously optically channeling the respective first and second light beams; and
   image generating means for generating a first image from the optically channeled first light beam and for nearly simultaneously generating a second image from the optically channeled second light beam.

13. The imaging flow cytometer of claim 12, further comprising:
   monitoring means for detecting when one of the at least one particles is within a predetermined imaging area.

14. The imaging flow cytometer of claim 13, further comprising:
   shutter means for passing the optically channeled first and second light to the image generating means, the shutter means being opened to pass the first and second light in response to the monitoring means detecting that one of the at least one particles is within the predetermined imaging area.

15. The imaging flow cytometer of claim 14, wherein the shutter means is an image intensifier which further amplifies the optically channeled first and second light prior to passage to the image generating means.

16. The imaging flow cytometer of claim 14, wherein the light emitting means is a continuous wave (CW) laser.

17. The imaging flow cytometer of claim 13, wherein the light emitting means includes a first continuous light source for emitting light to be detected by the monitoring means and a second pulsed laser light source for, upon the monitoring means detecting that one of the at least one particles is within a predetermined imaging area, being activated to emit light onto the transparent flow cell for subsequent generation of the first and second images.

18. The imaging flow cytometer of claim 12, wherein the light emitting means emits fluorescence exciting light onto the flow cell and the image generating means generates a first and second fluorescence image.

19. The imaging flow cytometer of claim 18, wherein the at least one particle in the transparent flow cell is preprocessed with a reagent causing fluorescence.

20. The imaging flow cytometer of claim 12, wherein each of the first and second optically channeling means include a lens for focusing the respective first and second light and a mirror for deflecting the respective focused first and second light.

21. The imaging flow cytometer of claim 20, further comprising:

common mirror for receiving each of the respective deflected first and second light from the mirror of the respective first and second optical channeling means, the common mirror further deflecting the received reflected first and second light to the image generating means.

* * * * *